United States Patent
Schall et al.

(10) Patent No.: US 7,490,749 B2
(45) Date of Patent: *Feb. 17, 2009

(54) SURGICAL STAPLING AND CUTTING INSTRUMENT WITH MANUALLY RETRACTABLE FIRING MEMBER

(75) Inventors: Christopher J. Schall, Cincinnati, OH (US); Chad P. Boudreaux, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 19 days.

This patent is subject to a terminal disclaimer.

(21) Appl. No.: 11/729,355

(22) Filed: Mar. 28, 2007

(65) Prior Publication Data

US 2008/0237298 A1 Oct. 2, 2008

(51) Int. Cl.
*A61B 17/068* (2006.01)

(52) U.S. Cl. .................. 227/176.1; 227/19; 227/180.1; 606/139; 606/219

(58) Field of Classification Search .................... 227/19, 227/176.1, 175.1, 175.2, 180.1, 178.1; 606/139, 606/219
See application file for complete search history.

(56) References Cited

U.S. PATENT DOCUMENTS

| | | | |
|---|---|---|---|
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,500,024 A | 2/1985 | DiGiovanni et al. | |

(Continued)

FOREIGN PATENT DOCUMENTS

CA 2458946 A1 3/2003

(Continued)

OTHER PUBLICATIONS

U.S. Appl. No. 11/729,013, filed Mar. 28, 2007.

(Continued)

*Primary Examiner*—Scott A. Smith

(57) ABSTRACT

A surgical stapling and severing instrument particularly suited to endoscopic procedures incorporates a handle that produces separate closing and firing motions to actuate an end effector. In particular, the handle produces multiple firing strokes in order to reduce the required amount of force required to fire (i.e., staple and sever) the end effector. A linked transmission reduces the required handle longitudinal length, yet achieves a rigid, strong configuration when straightened for firing. A traction biased firing mechanism avoids binding in driving this straightened linked rack. The instrument further has a manually actuatable retraction system that does not require the use of additional springs or other mechanisms to generate retraction forces which must be overcome when generating the forces necessary to fire the device. In various embodiments, the retraction system provides a visual indication to the surgeon as to how far firing has progressed.

19 Claims, 25 Drawing Sheets

U.S. PATENT DOCUMENTS

| | | |
|---|---|---|
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,655,222 A | 4/1987 | Florez et al. |
| 4,671,445 A | 6/1987 | Barker et al. |
| 4,715,520 A | 12/1987 | Roehr, Jr. et al. |
| 4,728,020 A | 3/1988 | Green et al. |
| 4,754,909 A | 7/1988 | Barker et al. |
| 4,767,044 A | 8/1988 | Green |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,397,324 A | 3/1995 | Carroll et al. |
| 5,425,745 A | 6/1995 | Green et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,529,235 A | 6/1996 | Boiarski et al. |
| 5,535,934 A | 7/1996 | Boiarski et al. |
| 5,535,935 A | 7/1996 | Vidal et al. |
| 5,540,375 A | 7/1996 | Bolanos et al. |
| 5,547,117 A | 8/1996 | Hamblin et al. |
| 5,554,169 A | 9/1996 | Green et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,575,799 A | 11/1996 | Bolanos et al. |
| 5,577,654 A | 11/1996 | Bishop |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,711,472 A | 1/1998 | Bryan |
| 5,715,987 A | 2/1998 | Kelley et al. |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,732,871 A | 3/1998 | Clark et al. |
| 5,735,874 A | 4/1998 | Measamer et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,132 A | 7/1998 | Knodel et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson, IV et al. |
| 5,878,937 A | 3/1999 | Green et al. |
| 5,894,979 A | 4/1999 | Powell |
| 5,897,562 A | 4/1999 | Bolanos et al. |
| 5,901,895 A | 5/1999 | Heaton et al. |
| 5,911,353 A | 6/1999 | Bolanos et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,079,606 A | 6/2000 | Milliman et al. |
| 6,083,242 A | 7/2000 | Cook |

| | | | | | | |
|---|---|---|---|---|---|---|
| 6,086,600 | A | 7/2000 | Kortenbach | 7,143,924 B2 | 12/2006 | Scirica et al. |
| 6,102,271 | A | 8/2000 | Longo et al. | 7,143,925 B2 | 12/2006 | Shelton, IV et al. |
| 6,109,500 | A | 8/2000 | Alli et al. | 7,143,926 B2 * | 12/2006 | Shelton et al. ............ 227/177.1 |
| 6,117,158 | A | 9/2000 | Measamer et al. | 7,147,138 B2 | 12/2006 | Shelton, IV |
| 6,155,473 | A | 12/2000 | Tompkins et al. | 7,159,750 B2 | 1/2007 | Racenet et al. |
| 6,171,330 | B1 | 1/2001 | Benchetrit | 7,168,604 B2 | 1/2007 | Milliman et al. |
| 6,202,914 | B1 | 3/2001 | Geiste et al. | 7,188,758 B2 | 3/2007 | Viola et al. |
| 6,241,139 | B1 | 6/2001 | Milliman et al. | 7,210,609 B2 | 5/2007 | Leiboff et al. |
| 6,250,532 | B1 | 6/2001 | Green et al. | 7,213,736 B2 | 5/2007 | Wales et al. |
| 6,264,086 | B1 | 7/2001 | McGuckin, Jr. | 7,220,272 B2 | 5/2007 | Weadock |
| 6,264,087 | B1 | 7/2001 | Whitman | 7,225,964 B2 | 6/2007 | Mastri et al. |
| 6,273,897 | B1 | 8/2001 | Dalessandro et al. | 7,238,195 B2 | 7/2007 | Viola |
| 6,315,184 | B1 | 11/2001 | Whitman | 7,246,734 B2 | 7/2007 | Shelton, IV |
| 6,330,965 | B1 | 12/2001 | Milliman et al. | 7,258,262 B2 | 8/2007 | Mastri et al. |
| 6,387,113 | B1 | 5/2002 | Hawkins et al. | 7,303,107 B2 | 12/2007 | Milliman et al. |
| RE37,814 | E | 8/2002 | Allgeyer | 7,328,828 B2 | 2/2008 | Ortiz et al. |
| 6,443,973 | B1 | 9/2002 | Whitman | 7,354,447 B2 | 4/2008 | Shelton, IV et al. |
| 6,488,197 | B1 | 12/2002 | Whitman | 7,398,908 B2 | 7/2008 | Holsten et al. |
| 6,491,201 | B1 | 12/2002 | Whitman | 2002/0117534 A1 | 8/2002 | Green et al. |
| 6,505,768 | B2 | 1/2003 | Whitman | 2004/0006372 A1 | 1/2004 | Racenet et al. |
| 6,616,686 | B2 | 9/2003 | Coleman et al. | 2004/0094597 A1 | 5/2004 | Whitman et al. |
| 6,619,529 | B2 | 9/2003 | Green et al. | 2004/0108357 A1 | 6/2004 | Milliman et al. |
| 6,629,988 | B2 | 10/2003 | Weadock | 2004/0122471 A1 | 6/2004 | Toby et al. |
| 6,644,532 | B2 | 11/2003 | Green et al. | 2004/0164123 A1 | 8/2004 | Racenet et al. |
| 6,669,073 | B2 | 12/2003 | Milliman et al. | 2004/0167572 A1 | 8/2004 | Roth et al. |
| 6,681,978 | B2 | 1/2004 | Geiste et al. | 2004/0173659 A1 | 9/2004 | Green et al. |
| 6,681,979 | B2 | 1/2004 | Whitman | 2004/0222268 A1 | 11/2004 | Bilotti et al. |
| 6,695,199 | B2 | 2/2004 | Whitman | 2004/0232201 A1 | 11/2004 | Wenchell et al. |
| 6,698,643 | B2 | 3/2004 | Whitman | 2004/0243151 A1 | 12/2004 | Demmy et al. |
| 6,716,233 | B1 | 4/2004 | Whitman | 2004/0254608 A1 | 12/2004 | Huitema et al. |
| 6,755,338 | B2 | 6/2004 | Hahnen et al. | 2005/0023324 A1 | 2/2005 | Doll et al. |
| 6,773,438 | B1 | 8/2004 | Knodel et al. | 2005/0070958 A1 | 3/2005 | Swayze et al. |
| 6,786,382 | B1 | 9/2004 | Hoffman | 2005/0072827 A1 | 4/2005 | Mollenauer |
| 6,805,273 | B2 | 10/2004 | Bilotti et al. | 2005/0103819 A1 | 5/2005 | Racenet et al. |
| 6,817,508 | B1 | 11/2004 | Racenet et al. | 2005/0119669 A1 | 6/2005 | Demmy |
| 6,817,509 | B2 | 11/2004 | Geiste et al. | 2005/0125009 A1 | 6/2005 | Perry et al. |
| 6,830,174 | B2 | 12/2004 | Hillstead et al. | 2005/0143759 A1 | 6/2005 | Kelly |
| 6,843,403 | B2 | 1/2005 | Whitman | 2005/0145671 A1 | 7/2005 | Viola |
| RE38,708 | E | 3/2005 | Bolanos et al. | 2005/0184121 A1 | 8/2005 | Heinrich |
| 6,877,647 | B2 | 4/2005 | Green et al. | 2005/0187576 A1 | 8/2005 | Whitman et al. |
| 6,905,057 | B2 | 6/2005 | Swayze et al. | 2005/0189397 A1 | 9/2005 | Jankowski |
| 6,945,444 | B2 | 9/2005 | Gresham et al. | 2005/0216055 A1 | 9/2005 | Scirica et al. |
| 6,953,138 | B1 | 10/2005 | Dworak et al. | 2005/0263562 A1 | 12/2005 | Shelton, IV et al. |
| 6,953,139 | B2 | 10/2005 | Milliman et al. | 2005/0263563 A1 | 12/2005 | Racenet et al. |
| 6,964,363 | B2 | 11/2005 | Wales et al. | 2005/0274768 A1 | 12/2005 | Cummins et al. |
| 6,978,921 | B2 | 12/2005 | Shelton, IV et al. | 2006/0011699 A1 | 1/2006 | Olson et al. |
| 6,978,922 | B2 | 12/2005 | Bilotti et al. | 2006/0047307 A1 | 3/2006 | Ortiz et al. |
| 6,981,628 | B2 | 1/2006 | Wales | 2006/0047308 A1 | 3/2006 | Ortiz et al. |
| 6,986,451 | B1 | 1/2006 | Mastri et al. | 2006/0049229 A1 | 3/2006 | Milliman et al. |
| 6,988,649 | B2 | 1/2006 | Shelton, IV et al. | 2006/0052825 A1 | 3/2006 | Ransick et al. |
| 6,988,650 | B2 | 1/2006 | Schwemberger et al. | 2006/0060630 A1 | 3/2006 | Shelton, IV et al. |
| 7,000,818 | B2 | 2/2006 | Shelton, IV et al. | 2006/0085033 A1 | 4/2006 | Criscuolo et al. |
| 7,000,819 | B2 | 2/2006 | Swayze et al. | 2006/0097026 A1 | 5/2006 | Shelton, IV |
| 7,008,435 | B2 | 3/2006 | Cummins | 2006/0100643 A1 | 5/2006 | Laufer et al. |
| 7,032,798 | B2 | 4/2006 | Whitman et al. | 2006/0151567 A1 | 7/2006 | Roy |
| 7,032,799 | B2 | 4/2006 | Viola et al. | 2006/0226196 A1 | 10/2006 | Hueil et al. |
| 7,044,352 | B2 | 5/2006 | Shelton, IV et al. | 2006/0278680 A1 | 12/2006 | Viola et al. |
| 7,044,353 | B2 | 5/2006 | Mastri et al. | 2006/0278681 A1 | 12/2006 | Viola et al. |
| 7,055,731 | B2 | 6/2006 | Shelton, IV et al. | 2006/0289602 A1 | 12/2006 | Wales et al. |
| 7,056,330 | B2 | 6/2006 | Gayton | 2007/0023477 A1 | 2/2007 | Whitman et al. |
| 7,059,508 | B2 | 6/2006 | Shelton, IV et al. | 2007/0034666 A1 | 2/2007 | Holsten et al. |
| 7,070,083 | B2 | 7/2006 | Jankowski | 2007/0045379 A1 | 3/2007 | Shelton, IV |
| 7,077,856 | B2 | 7/2006 | Whitman | 2007/0073340 A1 | 3/2007 | Shelton, IV et al. |
| 7,083,075 | B2 | 8/2006 | Swayze et al. | 2007/0075114 A1 | 4/2007 | Shelton, IV et al. |
| 7,090,684 | B2 | 8/2006 | McGuckin, Jr. et al. | 2007/0083234 A1 | 4/2007 | Shelton, IV et al. |
| 7,097,089 | B2 | 8/2006 | Marczyk | 2007/0084897 A1 | 4/2007 | Shelton, IV et al. |
| 7,108,709 | B2 | 9/2006 | Cummins | 2007/0102452 A1 | 5/2007 | Shelton, IV et al. |
| 7,111,769 | B2 | 9/2006 | Wales et al. | 2007/0102453 A1 | 5/2007 | Morgan et al. |
| 7,114,642 | B2 | 10/2006 | Whitman | 2007/0102472 A1 | 5/2007 | Shelton, IV |
| 7,118,582 | B1 | 10/2006 | Wang et al. | 2007/0102473 A1 | 5/2007 | Shelton, IV et al. |
| 7,128,253 | B2 | 10/2006 | Mastri et al. | 2007/0102474 A1 | 5/2007 | Shelton, IV et al. |
| 7,140,527 | B2 | 11/2006 | Ehrenfels et al. | 2007/0106317 A1 | 5/2007 | Shelton, IV et al. |
| 7,143,923 | B2 | 12/2006 | Shelton, IV et al. | 2007/0114261 A1 | 5/2007 | Ortiz et al. |

| | | | | | | |
|---|---|---|---|---|---|---|
| 2007/0158385 A1 | 7/2007 | Hueil et al. | | EP | 0033548 B1 | 5/1986 |
| 2007/0170225 A1 | 7/2007 | Shelton, IV et al. | | EP | 0639349 A2 | 2/1994 |
| 2007/0175949 A1 | 8/2007 | Shelton, IV et al. | | EP | 0593920 A1 | 4/1994 |
| 2007/0175950 A1 | 8/2007 | Shelton, IV et al. | | EP | 0600182 A2 | 6/1994 |
| 2007/0175951 A1 | 8/2007 | Shelton, IV et al. | | EP | 0630612 B1 | 12/1994 |
| 2007/0175952 A1 | 8/2007 | Shelton, IV et al. | | EP | 0634144 A1 | 1/1995 |
| 2007/0175953 A1 | 8/2007 | Shelton, IV et al. | | EP | 0646356 A2 | 4/1995 |
| 2007/0175955 A1 | 8/2007 | Shelton, IV et al. | | EP | 0646357 A1 | 4/1995 |
| 2007/0175956 A1 | 8/2007 | Swayze et al. | | EP | 0669104 A1 | 8/1995 |
| 2007/0175957 A1 | 8/2007 | Shelton, IV et al. | | EP | 0679367 A2 | 11/1995 |
| 2007/0175958 A1 | 8/2007 | Shelton, IV et al. | | EP | 0392547 B1 | 12/1995 |
| 2007/0175959 A1 | 8/2007 | Shelton, IV et al. | | EP | 0685204 A1 | 12/1995 |
| 2007/0175960 A1 | 8/2007 | Shelton, IV et al. | | EP | 0699418 A1 | 3/1996 |
| 2007/0175961 A1 | 8/2007 | Shelton, IV et al. | | EP | 0702937 A1 | 3/1996 |
| 2007/0175962 A1 | 8/2007 | Shelton, IV et al. | | EP | 0705571 A1 | 4/1996 |
| 2007/0175964 A1 | 8/2007 | Shelton, IV et al. | | EP | 0484677 B2 | 6/1996 |
| 2007/0179476 A1 | 8/2007 | Shelton, IV et al. | | EP | 0541987 B1 | 7/1996 |
| 2007/0194079 A1 | 8/2007 | Hueil et al. | | EP | 0667119 B1 | 7/1996 |
| 2007/0194080 A1 | 8/2007 | Swayze et al. | | EP | 0770355 A1 | 5/1997 |
| 2007/0194081 A1 | 8/2007 | Hueil et al. | | EP | 0503662 B1 | 6/1997 |
| 2007/0194082 A1 | 8/2007 | Morgan et al. | | EP | 0625335 B1 | 11/1997 |
| 2007/0233053 A1 | 10/2007 | Shelton, IV et al. | | EP | 0552423 B1 | 1/1998 |
| 2007/0262116 A1 | 11/2007 | Hueil et al. | | EP | 0592244 B1 | 1/1998 |
| 2007/0295780 A1 | 12/2007 | Shelton et al. | | EP | 0648476 B1 | 1/1998 |
| 2008/0029570 A1 | 2/2008 | Shelton et al. | | EP | 0603472 B1 | 11/1998 |
| 2008/0029571 A1 | 2/2008 | Shelton et al. | | EP | 0878169 A1 | 11/1998 |
| 2008/0029572 A1 | 2/2008 | Shelton et al. | | EP | 0760230 B1 | 2/1999 |
| 2008/0029573 A1 | 2/2008 | Shelton et al. | | EP | 0537572 B1 | 6/1999 |
| 2008/0029574 A1 | 2/2008 | Shelton et al. | | EP | 0552050 B1 | 5/2000 |
| 2008/0029575 A1 | 2/2008 | Shelton et al. | | EP | 1090592 A1 | 4/2001 |
| 2008/0029576 A1 | 2/2008 | Shelton et al. | | EP | 1256318 B1 | 5/2001 |
| 2008/0029577 A1 | 2/2008 | Shelton et al. | | EP | 0908152 B1 | 1/2002 |
| 2008/0035701 A1 | 2/2008 | Racenet et al. | | EP | 0872213 B1 | 5/2002 |
| 2008/0041917 A1 | 2/2008 | Racenet et al. | | EP | 1238634 A2 | 9/2002 |
| 2008/0078800 A1 | 4/2008 | Hess et al. | | EP | 0656188 B1 | 1/2003 |
| 2008/0078801 A1 | 4/2008 | Shelton et al. | | EP | 0829235 B1 | 6/2003 |
| 2008/0078802 A1 | 4/2008 | Hess et al. | | EP | 0813843 B1 | 10/2003 |
| 2008/0078803 A1 | 4/2008 | Shelton et al. | | EP | 0705570 B1 | 4/2004 |
| 2008/0078804 A1 | 4/2008 | Shelton et al. | | EP | 1086713 B1 | 5/2004 |
| 2008/0078805 A1 | 4/2008 | Omaits et al. | | EP | 1426012 A1 | 6/2004 |
| 2008/0078806 A1 | 4/2008 | Omaits et al. | | EP | 0888749 B1 | 9/2004 |
| 2008/0078807 A1 | 4/2008 | Hess et al. | | EP | 1477119 A1 | 11/2004 |
| 2008/0078808 A1 | 4/2008 | Hess et al. | | EP | 1479345 A1 | 11/2004 |
| 2008/0082115 A1 | 4/2008 | Morgan et al. | | EP | 1479347 A1 | 11/2004 |
| 2008/0082124 A1 | 4/2008 | Hess et al. | | EP | 1479348 A1 | 11/2004 |
| 2008/0082125 A1 | 4/2008 | Murray et al. | | EP | 1520523 A1 | 4/2005 |
| 2008/0082126 A1 | 4/2008 | Murray et al. | | EP | 1520525 A1 | 4/2005 |
| 2008/0164296 A1 | 7/2008 | Shelton et al. | | EP | 1522264 A1 | 4/2005 |
| 2008/0167522 A1 | 7/2008 | Giordano et al. | | EP | 1550408 A1 | 7/2005 |
| 2008/0167644 A1 | 7/2008 | Shelton et al. | | EP | 1557129 A1 | 7/2005 |
| 2008/0167670 A1 | 7/2008 | Shelton et al. | | EP | 1064883 B1 | 8/2005 |
| 2008/0167671 A1 | 7/2008 | Giordano et al. | | EP | 1621141 A2 | 2/2006 |
| 2008/0167672 A1 | 7/2008 | Giordano et al. | | EP | 1652481 A2 | 5/2006 |
| 2008/0167736 A1 | 7/2008 | Swayze et al. | | EP | 1382303 B1 | 6/2006 |
| 2008/0169327 A1 | 7/2008 | Shelton et al. | | EP | 1045672 B1 | 8/2006 |
| 2008/0169328 A1 | 7/2008 | Shelton | | EP | 1617768 B1 | 8/2006 |
| 2008/0169329 A1 | 7/2008 | Shelton et al. | | EP | 1702567 A2 | 9/2006 |
| 2008/0169330 A1 | 7/2008 | Shelton et al. | | EP | 1129665 B1 | 11/2006 |
| 2008/0169331 A1 | 7/2008 | Shelton et al. | | EP | 1256317 B1 | 12/2006 |
| 2008/0169332 A1 | 7/2008 | Shelton et al. | | EP | 1728473 A1 | 12/2006 |
| 2008/0169333 A1 | 7/2008 | Shelton et al. | | EP | 1728475 A2 | 12/2006 |
| | | | | EP | 1479346 B1 | 1/2007 |
| | FOREIGN PATENT DOCUMENTS | | | EP | 1484024 B1 | 1/2007 |
| | | | | EP | 1300117 B1 | 8/2007 |
| CA | 2512960 A1 | 1/2006 | | FR | 1112936 A | 3/1956 |
| CA | 2514274 A1 | 1/2006 | | GB | 939929 A | 10/1963 |
| DE | 273689 C | 5/1914 | | GB | 2336214 A | 10/1999 |
| DE | 9412228 U | 9/1994 | | JP | 6007357 A | 1/1994 |
| DE | 69328576 T2 | 1/2001 | | JP | 7051273 A | 2/1995 |
| DE | 20112837 U1 | 10/2001 | | JP | 8033641 A | 2/1996 |
| DE | 20121753 U1 | 4/2003 | | JP | 8229050 A | 9/1996 |
| DE | 10314072 A1 | 10/2004 | | JP | 2001286477 A | 10/2001 |
| EP | 0122046 A1 | 10/1984 | | JP | 2002369820 A | 12/2002 |

| | | | |
|---|---|---|---|
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/29639 A1 | 11/1995 |
| WO | WO 96/35464 A1 | 11/1996 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105702 A2 | 12/2003 |
| WO | WO 2004/006980 A2 | 1/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

* cited by examiner

SURGICAL STAPLING AND CUTTING INSTRUMENT WITH MANUALLY RETRACTABLE FIRING MEMBER

CROSS REFERENCE TO RELATED APPLICATIONS

The present application is related to commonly-owned U.S. patent application Ser. No. 11/729,013, to Chad P. Boudreaux and Christopher J. Schall, filed Mar. 28, 2007, entitled "Surgical Stapling and Cutting Instrument With Side Mounted Refraction Member", the disclosure of which is hereby incorporated by reference in its entirety.

FIELD OF THE INVENTION

The present invention relates in general to endoscopic surgical instruments including, but not limited to, surgical stapler instruments that are capable of applying lines of staples to tissue while cutting the tissue between those staple lines and, more particularly, to improvements relating to surgical stapler instruments and improvements in processes for forming various components of such surgical stapler instruments that have manual retraction capabilities.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895 to Brian D. Knodel, Richard P. Nuchols, and Warren P. Williamson, IV, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever or staple.

One specific advantage of being able to close upon tissue before firing is that the clinician is able to verify via an endoscope that the desired location for the cut has been achieved, including that a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Generally, a single closing stroke followed by a single firing stroke is a convenient and efficient way to perform severing and stapling. However, in some instances, it would be desirable for multiple firing strokes to be required. For example, surgeons are able to select a length of staple cartridge for the desired length of cut from a range of jaw sizes. Longer staple cartridges require a longer firing stroke. Thus, to effect the firing, a hand-squeezed trigger is required to exert a larger force for these longer staple cartridges in order to sever more tissue and drive more staples as compared to a shorter staple cartridge. It would be desirable for the amount of force to be lower and comparable to shorter cartridges so as not to exceed the hand strength of some surgeons. In addition, some surgeons, not familiar with the larger staple cartridges, may become concerned that binding or other malfunction has occurred when an unexpectedly higher force is required.

One approach for lowering the required force for a firing stroke is a ratcheting mechanism that allows a firing trigger to be stroked multiple times, as described in U.S. Pat. Nos. 5,762,256 and 6,330,965, the disclosures of which are herein incorporated by reference. These known surgical stapling instruments with multiple-stroke firing mechanisms do not have the advantages of a separate closure and firing actions.

Other ratcheting surgical instruments are disclosed in commonly-owned U.S. Pat. No. 7,083,075, issued Aug. 1, 2006 to Jeffrey S. Swayze, Frederick E. Shelton, IV, Kevin Ross Doll, and Douglass B. Hoffman, entitled Multi-Stroke Mechanism With Automatic End of Stroke Retraction, which is hereby incorporated by reference. Various embodiments disclosed therein employ a handle that produces separate closing and firing motions to actuate an end effector. In particular, the handle is configured to generate the firing force necessary to staple and sever the tissue clamped within the end effector through multiple actuations of a firing trigger. The device may further employ a linked transmission which reduces the required handle length, yet achieves a rigid, strong configuration when straightened for firing. A traction biased firing mechanism avoids binding in driving this straightened linked rack in cooperation with an anti-backup mechanism, with a lockout mechanism that prevents releasing the closure trigger during firing. Furthermore, an external indicator gives feedback to the surgeon as to how far firing has progressed, as well as providing a manual retraction capability. These embodiments also generally employ a relatively strong spring to automatically retract the cutting member after the end effector has been fired. While such designs are extremely effective, the use of the retraction spring requires additional firing force to be generated to overcome the opposing spring force during firing. This problem can also be somewhat exacerbated when using articulating end effectors. In particular, when an articulating end effector is employed, a larger return spring must generally be employed to retract the articulating firing member. Use of such larger spring further increases the amount of firing forces that must be generated to overcome the spring force and fire the end effector components.

Consequently, a significant need exists for a surgical stapling instrument having a multiple stroke or other type of firing mechanism that is equipped with a manually actuatable retraction mechanism and does not employ an additional retraction means such as a spring or the like that generates forces that must be overcome during the firing stroke.

SUMMARY

In one aspect of the invention, there is provided a surgical instrument has a handle assembly and an end effector for performing a surgical operation. The end effector is operably coupled to the handle assembly and may operably support a firing member that is movable from a retracted position to a fired position in response to a longitudinal firing motion applied thereto. The instrument may also include a firing drive that is supported by the handle assembly and is configured to selectively generate the longitudinal firing motion upon actuation of a firing trigger operably coupled to the handle assembly. A retraction assembly may be supported by the handle assembly and interface with the firing drive such that manual actuation of the retraction assembly causes the firing drive to apply a sole retraction motion which is communicated to the firing member to cause the firing member to move from the fired position to the retracted position.

In another general aspect of various embodiments of the present invention there is provided a surgical instrument that has a handle assembly that is coupled to an end effector for performing a surgical operation. The end effector may operably support a firing member that is movable from a retracted position to a fired position in response to a longitudinal firing motion applied thereto. A linked rack may be operably supported by the handle assembly and a firing rod may communicate with the linked rack and the end effector for transmitting the firing and retraction motions from the linked rack to the end effector. A firing trigger may be operably supported by the handle assembly and may be configured to interface with the linked rack such that actuation of the firing trigger causes the linked rack to apply the firing motion to the firing rod. A first gear may be in meshing engagement with the linked rack and a retraction lever may be movably supported by the handle assembly and may be configured to interface with the first gear such that actuation of the retraction lever applies the sole retraction motion or force to the first gear which thereby transfers the sole retraction motion to the linked rack.

In still another general aspect of various embodiments of the present invention there is provided a surgical instrument that has a handle assembly that is coupled to an end effector. The end effector may operably support a firing member that is movable from a retracted position to a fired position in response to a longitudinal firing motion applied thereto. A first linked rack may be operably supported by the handle assembly. A firing rod may communicate with the linked rack and the end effector for transmitting the firing and retraction motions from the linked rack to the end effector. A firing trigger may be operably supported by the handle assembly and may be configured to selectively interface with the linked rack such that actuation of the firing trigger causes the linked rack to apply the firing motion to the firing rod. A second gear rack may be operably supported by the handle assembly. A drive gear may be in meshing engagement with the first linked rack and the second gear rack. A retraction lever may be movably coupled to the handle assembly and the second gear rack such that actuation of the retraction lever applies the sole retraction motion to the drive gear which thereby transfers the sole retraction motion to the linked rack.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Figure 1:
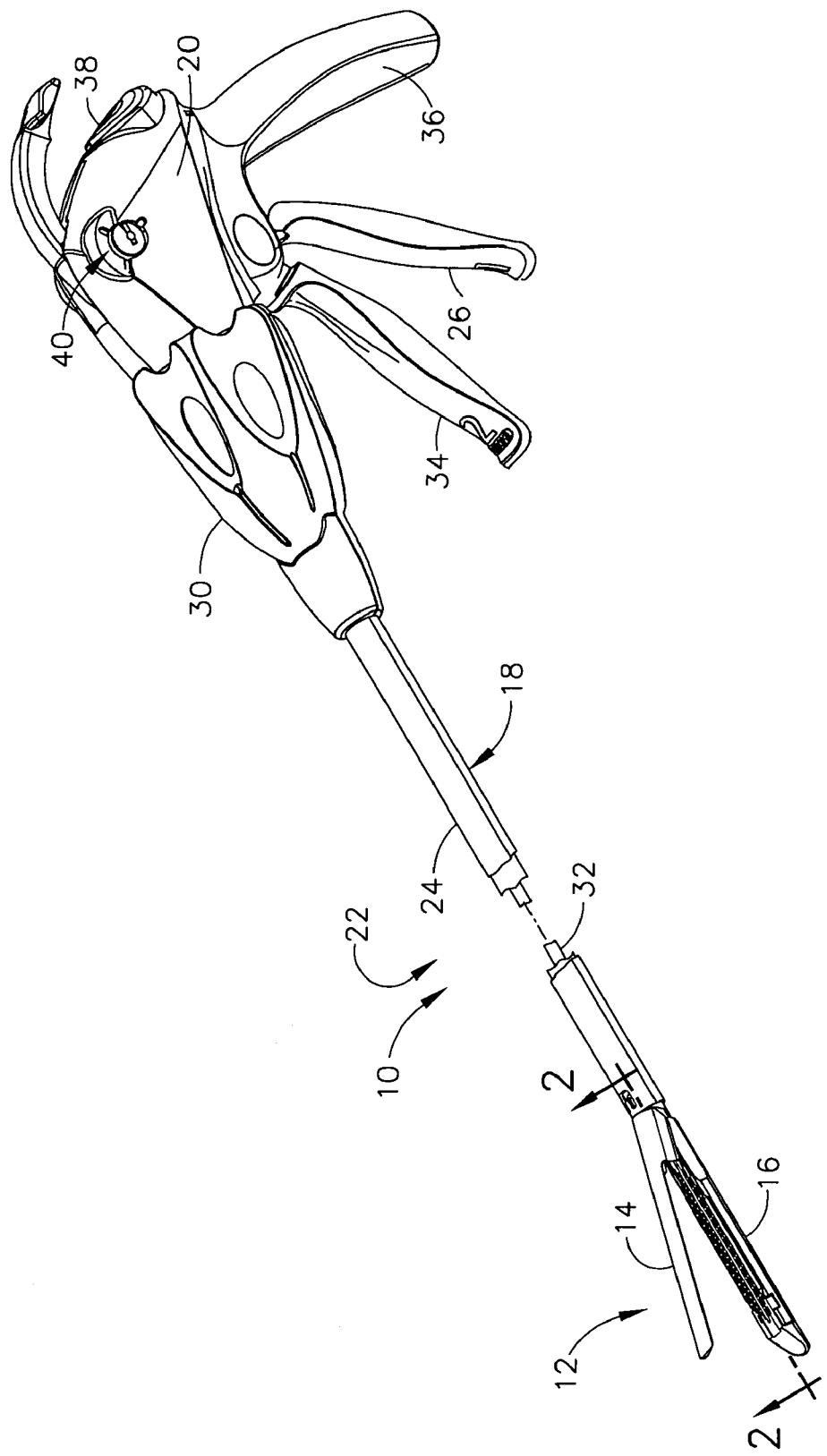
FIG. 1 is a perspective view of a surgical stapling and severing instrument of various embodiments of the present invention.
Figure 2:
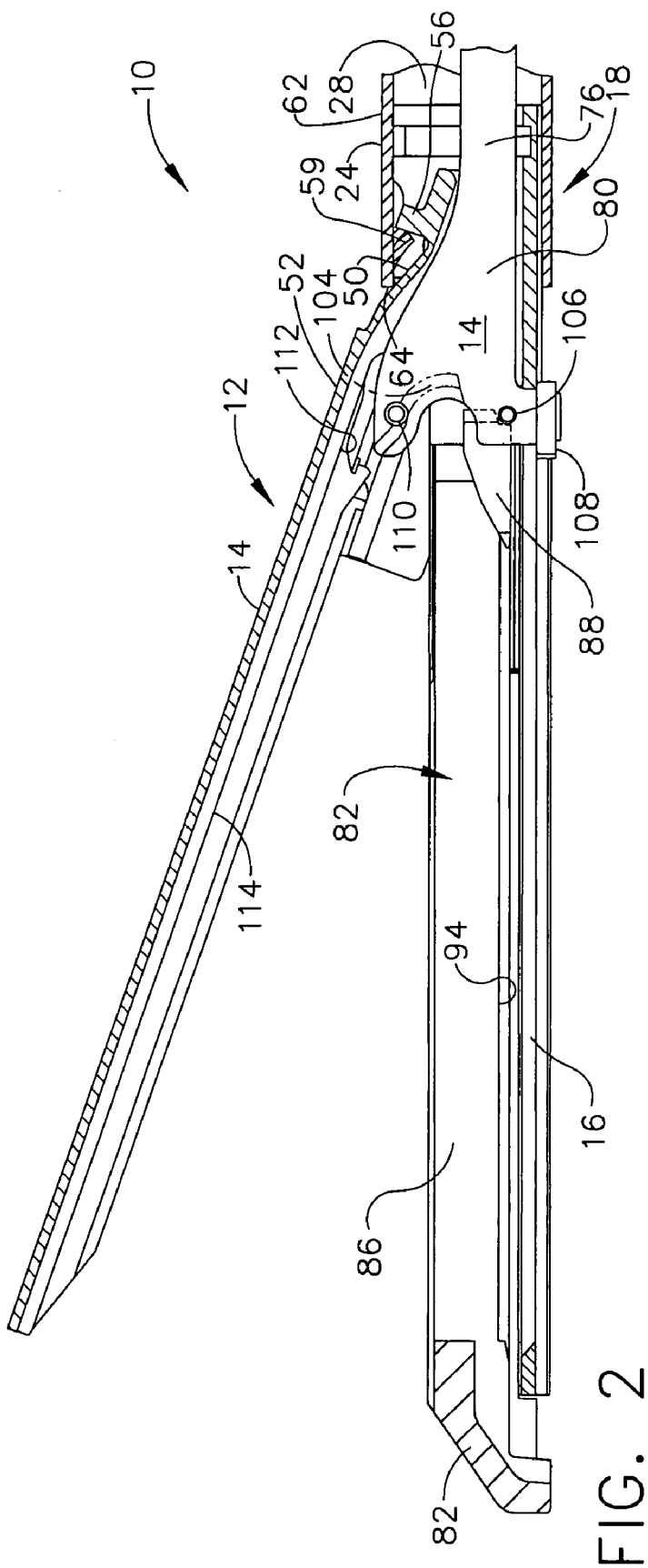
FIG. 2 is a left side elevation view taken along line 2-2 in longitudinal cross section of an end effector at a distal portion of the surgical stapling instrument of FIG. 1.

Turning to the Drawings, wherein like numerals denote like components throughout the several views, FIGS. 1 and 2 depict a surgical stapling and severing instrument 10 that is capable of practicing the unique benefits of the present invention. The surgical stapling and severing instrument 10 may incorporate an end effector 12 having an anvil 14 that is pivotally attached to an elongate channel 16, forming opposing jaws for clamping tissue to be severed and stapled. The end effector 12 may be coupled by an elongate shaft assembly 18 to a handle 20 (FIG. 1). An implement portion 22, formed by the end effector 12 and shaft assembly 18, is advantageously sized for insertion through a trocar or small laparoscopic opening to perform an endoscopic surgical procedure while being controlled by a surgeon grasping the handle assembly 20. The handle assembly 20 may advantageously include features that allow separate closure motions and firing motions, lockouts to prevent inadvertent or ill-advised firing of the end effector, as well as enabling multiple firing strokes to effect firing (i.e., severing and stapling) of the end effector 12 while indicating the degree of firing to the surgeon. In addition, as will be described in detail below, various embodiments may employ a unique and novel manually actuatable retraction mechanism for retracting the firing members without any assistance from a retraction spring or other retraction arrangement, the forces of which must be overcome during the firing operation.

To these ends, a closure tube 24 of the shaft assembly 18 is coupled between a closure trigger 26 (FIG. 1) and the anvil 14 to cause closure of the end effector 12. Within the closure tube 24, a frame 28 is coupled between the elongate channel 16 and the handle assembly 20 to longitudinally position and support the end effector 12. A rotation knob 30 may be coupled with the frame 28, and both elements are rotatably coupled to the handle assembly 20 with respect to a rotational movement about a longitudinal axis of the shaft assembly 18. Thus, the surgeon can rotate the end effector 12 by turning the rotation knob 30. The closure tube 24 is also rotated by the rotation knob 30 but retains a degree of longitudinal movement relative thereto to cause the closure of the end effector 12. Within the frame 28, a firing rod 32 is positioned for longitudinal movement and coupled between the anvil 14 of the end effector 12 and a multiple-stroke firing trigger 34. The closure trigger 26 is distal to a pistol grip 36 of the handle assembly 20 with the firing trigger 34 distal to both the pistol grip 36 and closure trigger 26.

In endoscopic operation, once the implement portion 22 is inserted into a patient to access a surgical site, a surgeon may refer to an endoscopic or other diagnostic imaging device to position tissue between the anvil 14 and elongate channel 16. Grasping the closure trigger 26 and pistol grip 36, the surgeon may repeatedly grasp and position the tissue. Once satisfied as to the location of the tissue relative to the end effector 12 and the amount of tissue therein, the surgeon depresses the closure trigger 26 fully toward the pistol grip 36, clamping the tissue in the end effector 12 and locking the closure trigger 26 in this clamped (closed) position. If not satisfied with this position, the surgeon may release the closure trigger 26 by depressing a closure release button 38 and thereafter repeat the procedure to clamp tissue.

If the clamping is correct, the surgeon may proceed with firing the surgical stapling and severing instrument 10. Specifically, the surgeon grasps the firing trigger 34 and pistol grip 36, depressing the firing trigger 34 a predetermined number of times. The number of firing strokes necessary may be ergonomically determined based on a maximum hand size, maximum amount of force to be imparted to the instrument during each firing stroke, and the longitudinal distance and force needed to be transferred through the firing rod 32 to the end effector 12 during firing.

During these strokes, the surgeon may reference an indicator, depicted as an indicating knob 40, that positionally rotates in response to the multiple firing strokes. Additionally, the position of the indicating knob 40 may confirm that full firing has occurred when encountering resistance to further cycling of the firing trigger 34. It should be appreciated that various indicia and instructions may be added to the handle assembly 20 to enhance the indication provided by the rotation of the indicating knob 40.

It will be appreciated that the terms "proximal" and "distal" are used herein with reference to a clinician gripping a handle of an instrument. Thus, the end effector 12 is distal with respect to the more proximal handle assembly 20. Analogous terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The present invention is being discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

E-Beam Firing Member

Figure 3:
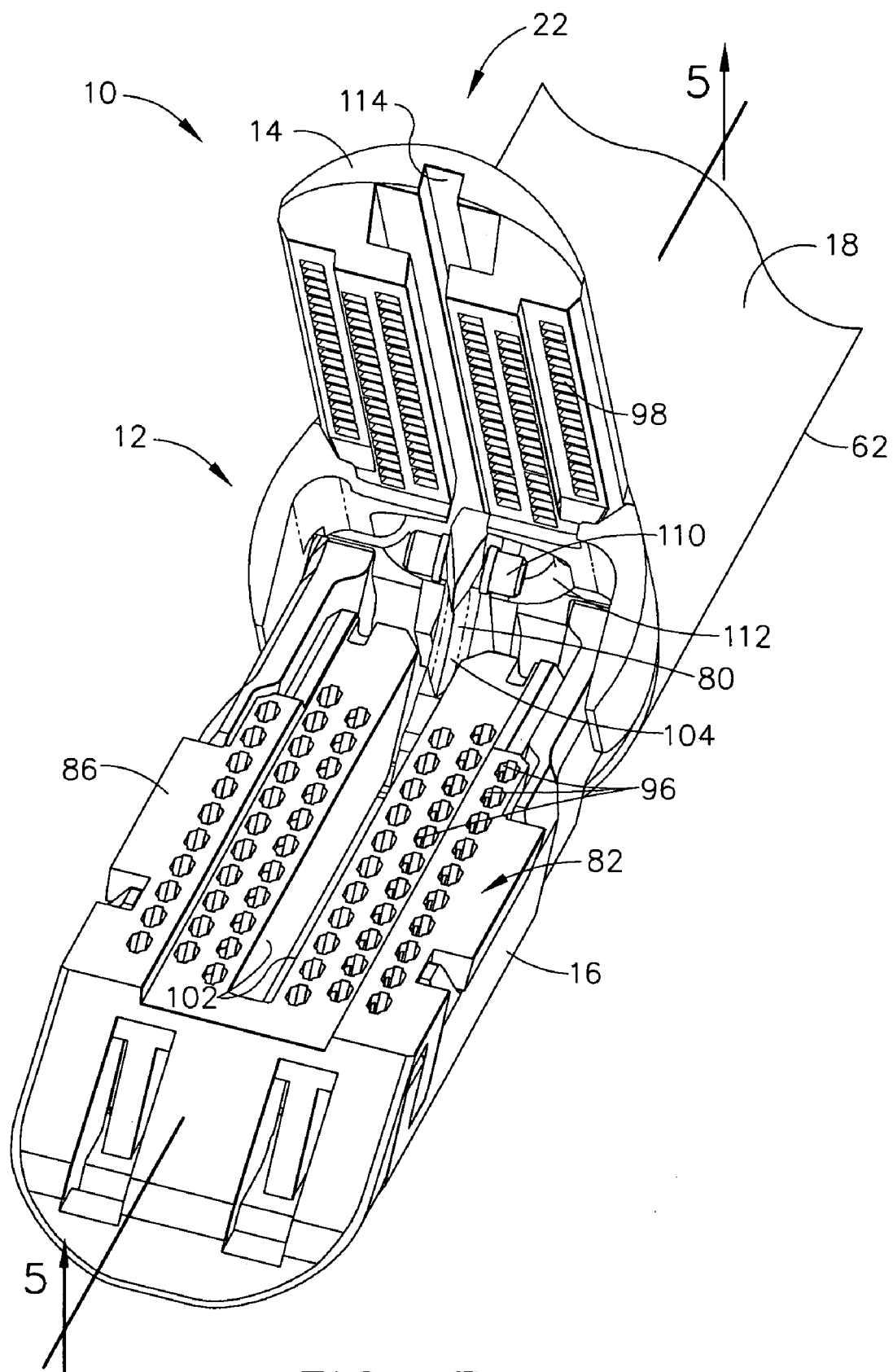
FIG. 3 is a front perspective view of the end effector of FIG. 2.
Figure 4:
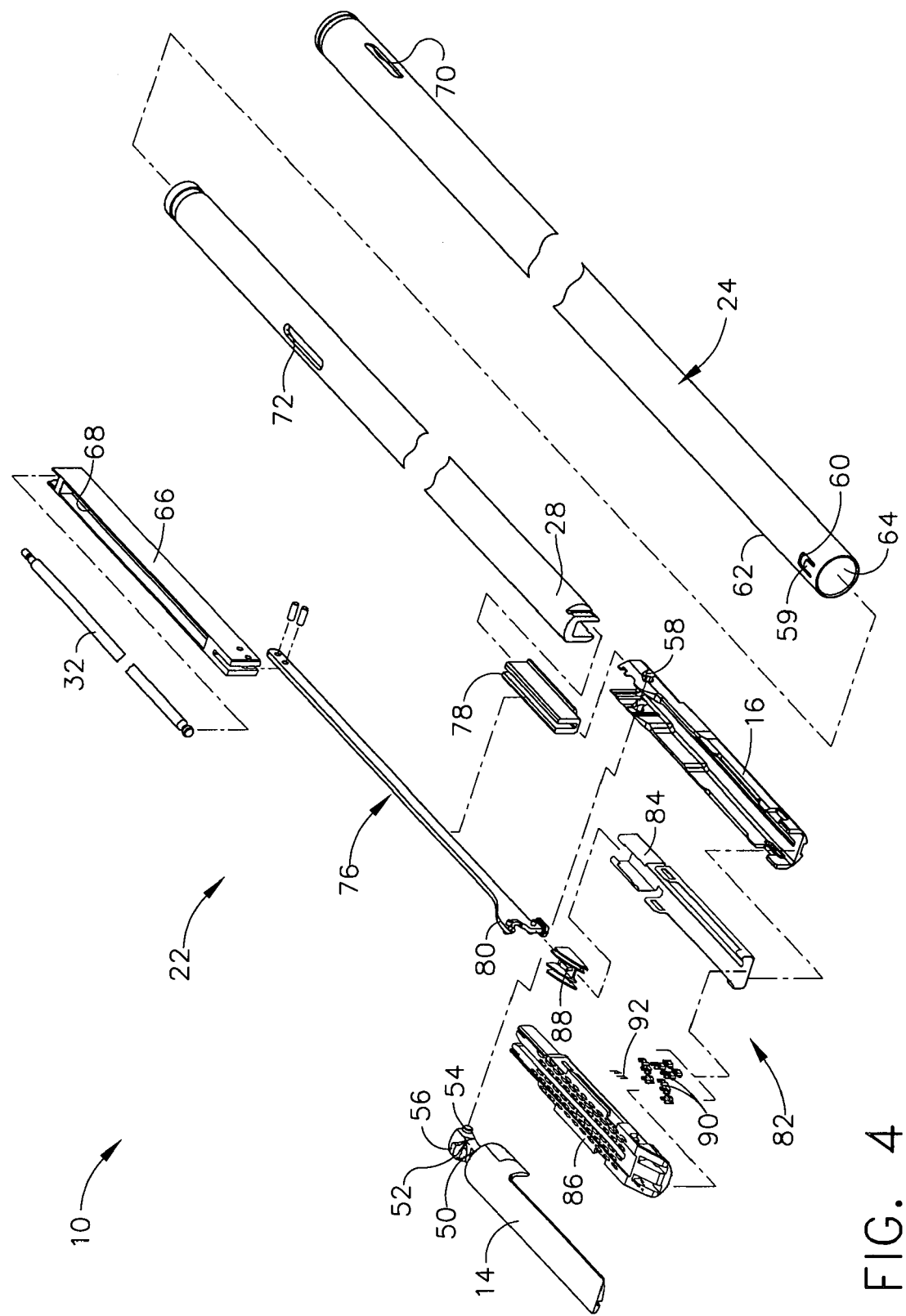
FIG. 4 is a perspective, exploded view of an implement portion of the surgical stapling and severing instrument of FIG. 1.

The advantages of a handle assembly 20, which is capable of providing multiple-stroke firing motion, has application to a number of instruments, with one such end effector 12 being depicted in FIGS. 2-6. With particular reference to FIG. 4, the end effector 12 responds to the closure motion from the handle assembly 20 (not depicted in FIGS. 2-6) first by including an anvil face 50 (FIGS. 2, 4, 6) connecting to an anvil proximal end 52 that includes a pair of laterally projecting anvil pivot pins 54 that are proximal to a vertically projecting anvil feature 56 (FIG. 4). The anvil pivot pins 54 translate within kidney shaped openings 58 in the elongate channel 16 to open and close anvil 14 relative to elongate channel 16. The anvil feature 56 engages a tab 59 (FIGS. 2, 4, 6) extending inwardly in tab aperture 60 on a distal end 62 of the closure tube 24, the latter distally terminating in a distal edge 64 that pushes against the anvil face 50. Thus, when the closure tube 24 moves proximally from its open position, the tab 59 of the closure tube 24 draws the anvil feature 56 proximally, and the anvil pivot pins 54 follow the kidney shaped openings 58 of the elongate channel 16 causing the anvil 14 to simultaneously translate proximally and rotate upward to the open position. When the closure tube 24 moves distally, the tab 59 in the tab aperture 60 releases from the anvil feature 56 and the distal edge 64 pushes on the anvil face 50, closing the anvil 14.

With continued reference to FIG. 4, the implement portion 22 also includes components that respond to the firing motion of the firing rod 32. In particular, the firing rod 32 rotatably engages a firing trough member 66 having a longitudinal recess 68. Firing trough member 66 moves longitudinally within frame 28 in direct response to longitudinal motion of firing rod 32. A longitudinal slot 70 in the closure tube 24 operably couples with the rotation knob 30 (not shown in FIGS. 2-6). The length of the longitudinal slot 70 in the closure tube 24 is sufficiently long to allow relative longitudinal motion with the rotation knob 30 to accomplish firing and closure motions respectively with the coupling of the rotation knob 30 passing on through a longitudinal slot 72 in the frame 28 to slidingly engage the longitudinal recess 68 in the frame trough member 66.

The distal end of the frame trough member 66 is attached to a proximal end of a firing bar 76 that moves within the frame 28, specifically within a guide 78 therein, to distally project an E-beam firing member 80 into the end effector 12. The end effector 12 includes a staple cartridge 82 that is actuated by the E-beam 80. The staple cartridge 82 has a tray 84 that holds a staple cartridge body 86, a wedge sled driver 88, staple drivers 90 and staples 92. It will be appreciated that the wedge sled driver 88 longitudinally moves within a firing recess 94 (FIG. 2) located between the cartridge tray 84 and the cartridge body 86. The wedge sled driver 88 presents camming surfaces that contact and lift the staple drivers 90 upward, driving the staples 92 up from staple apertures 96 (FIG. 3) into contact with staple forming grooves 98 (FIG. 3) of the anvil 14, creating formed "B"-shaped staples, such as depicted at 100 of FIG. 6. With particular reference to FIG. 3, the staple cartridge body 86 further includes a proximally open, vertical slot 102 for passage of the E-beam 80. Specifically, a cutting surface 104 is provided along a distal end of E-beam 80 to cut tissue after it is stapled.

Figure 5:
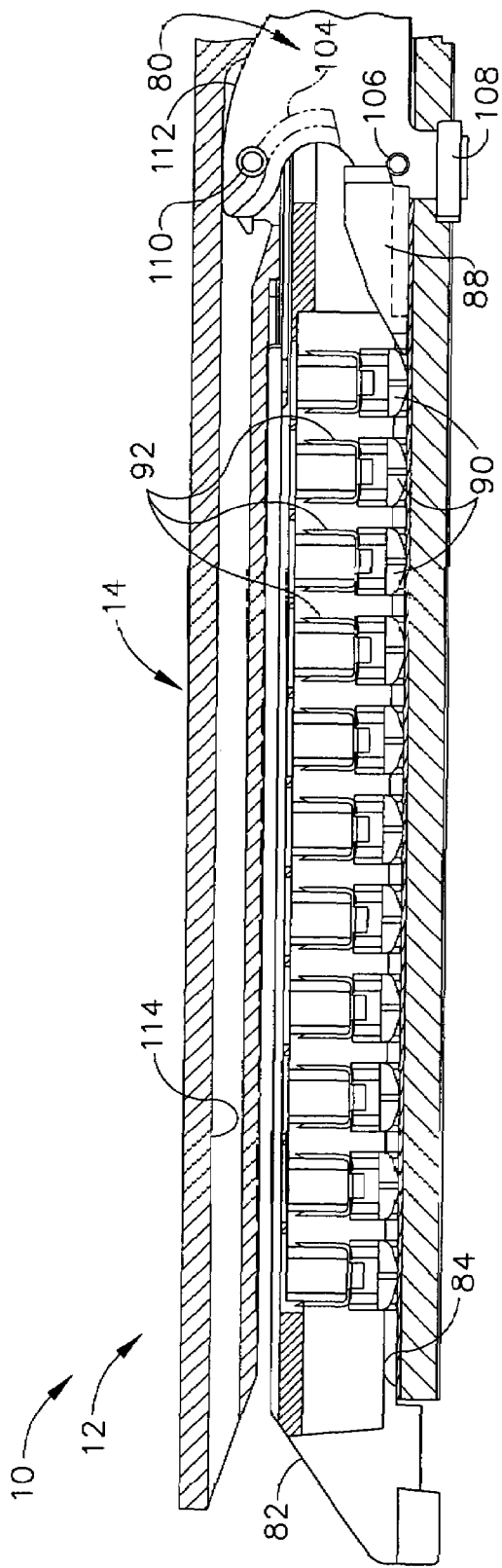
FIG. 5 depicts a left side elevation view in section of the end effector of FIG. 3 of the surgical instrument of FIG. 1, the section generally taken along lines 5-5 of FIG. 3 to expose portions of a staple cartridge but also depicting the firing bar along the longitudinal centerline.
Figure 6:
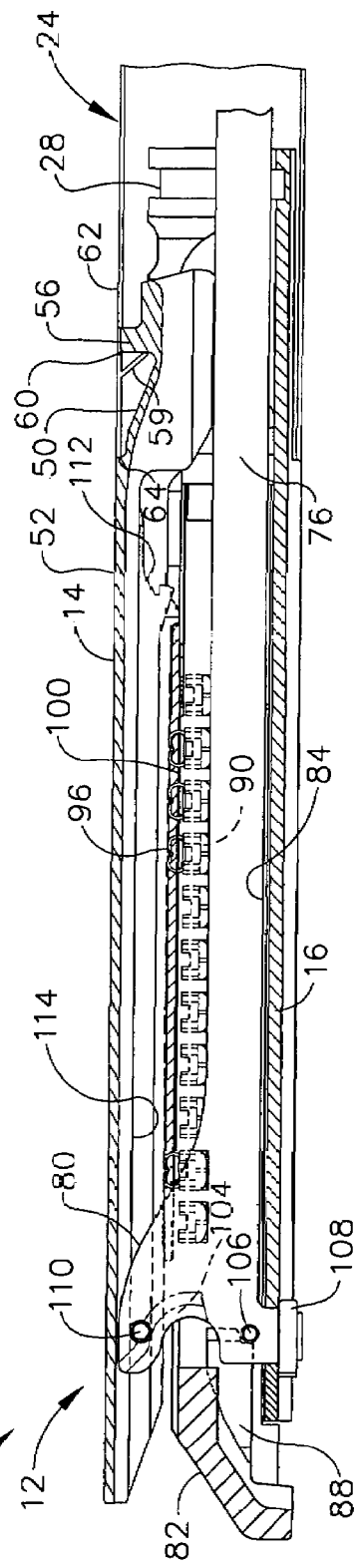
FIG. 6 depicts a left side elevation view in section of the end effector of FIG. 5 after the firing bar has fully fired.

In FIGS. 2, 5, 6, respectively, the end effector 12 is depicted in a sequence of open (i.e., start) condition, clamped and unfired condition or position, and fully fired condition or position. Features of the E-beam 80 that facilitate firing of the end effector 12, in particular, are depicted. In FIG. 2, the wedge sled driver 88 is in its fully proximal position, indicating an unfired staple cartridge 82. A middle pin 106 is aligned to enter the firing recess 94 in the staple cartridge 82, for distally driving the wedge sled driver 88. A bottom pin or cap 108 of the E-beam 80 slides along a bottom surface of the elongate channel 16, thus the middle and bottom pins 106, 108 slidingly engage the elongate channel 16. In the open and unfired state of FIG. 2, a top pin 110 of the E-beam 80 has entered and is residing within an anvil pocket 112 of the anvil 14, and thus does not impede repeated opening and closing of the anvil 14.

In FIG. 5, the end effector 12 is depicted as clamped and ready to fire. The top pin 110 of the E-beam 80 is aligned with an anvil slot 114 in the anvil 14 distal to and communicating with the anvil pocket 112. In FIG. 6, the E-beam 80 has been fully fired, with the upper pin 110 translating down the anvil slot 114, affirmatively spacing the anvil 14 from the elongate channel 16 as the cutting surface 104 severs clamped tissue. Simultaneously, the middle pin 106 has actuated the staple cartridge 82 as previously described. Thereafter, the E-beam 80 is retracted prior to opening the end effector 12 and replacing the staple cartridge 82 for an additional operation.

The illustrative end effector 12 is described in greater detail in four commonly-owned U.S. patents and a patent application, the disclosure of each being hereby incorporated by reference in their entirety: (1) U.S. Pat. No. 7,044,352 to Frederick E. Shelton IV, Michael E. Setser, William B. Weisenburgh II, issued May 16, 2006 and entitled "Surgical Stapling Instrument Having a Single Lockout Mechanism For Prevention of Firing"; (2) U.S. Pat. No. 7,000,818 to Frederick E. Shelton IV, Michael E. Setser, Brian J. Hemmelgarn II, issued Feb. 21, 2006 and entitled "Surgical Stapling Instrument Having Separate Distinct Closing and Firing Systems"; (3) U.S. Pat. No. 6,988,649 to Frederick E. Shelton IV, Michael E. Setser, and William B. Weisenburgh II, issued Jan. 24, 2006 and entitled "Surgical Stapling Instrument Having A Spent Cartridge Lockout"; (4) U.S. Pat. No. 7,143,923, to Frederick E. Shelton IV, Michael E. Setser, and William B. Weisenburgh II, issued Dec. 5, 2006 and entitled Surgical Stapling Instrument Having A Firing Lockout For An Unclosed Anvil"; and (5) U.S. patent application entitled "Surgical Stapling Instrument Incorporating an E-Beam Firing Mechanism", Ser. No. 10/443,617, to Frederick E. Shelton IV, Michael E. Setser, William B. Weisenburgh II, filed 20 June 2003, now U.S. Pat. No. 6,978,921. However, the unique and novel features of various embodiments of the present invention may also be employed with different types of end effectors without departing from the spirit and scope of the present invention.

It should be appreciated that although a nonarticulating shaft assembly 18 is illustrated herein, applications of the present invention may include instruments capable of articulation, such as those described in three commonly owned U.S. patents and two commonly owned U.S. patent applications, the disclosure of each being hereby incorporated by reference in their entirety: (1) U.S. Pat. No. 7,111,769 to Kenneth S. Wales, Douglas B. Hoffman, Frederick E. Shelton IV, and Jeffrey S. Swayze, issued Sept. 26, 2006, entitled "Surgical Instrument Incorporating An Articulation Mechanism Having Rotation About the Longitudinal Axis"; (2) U.S. Pat. No. 6,981,628 to Kenneth S. Wales, issued January 3, 2006, entitled "Surgical Instrument With A Lateral-Moving Articulation Control"; (3) U.S. Pat. No. 7,055,731 to Frederick E. Shelton IV, Michael E. Setser, William B. Weisenburgh II, issued June 6, 2006entitled "Surgical Stapling Instrument Incorporating A Tapered Firing Bar For Increased Flexibility Around The Articulation Joint"; (4) U.S. Patent Publication No. 2005/0006429entitled "Surgical Stapling Instrument Having Articulation Joint Support Plates For Supporting A Firing Bar", Ser. No. 10/615,971, to Kenneth S. Wales and Joseph Charles Hueil, filed 9 July 2003, now U.S. Pat. No.

6,964,363; and (5) U.S. patent application entitled "Surgical Stapling Instrument Incorporating An Articulation Joint For a Firing Bar Track", Ser. No. 10/615,962, to Brian J. Hemmelgarn, filed 9 July 2003. Those of ordinary skill in the art will readily understand, however, that the unique and novel aspects of various features of the present invention may be employed in connection with other types of articulating surgical instruments without departing from the spirit and scope of the present invention.

Figure 7:
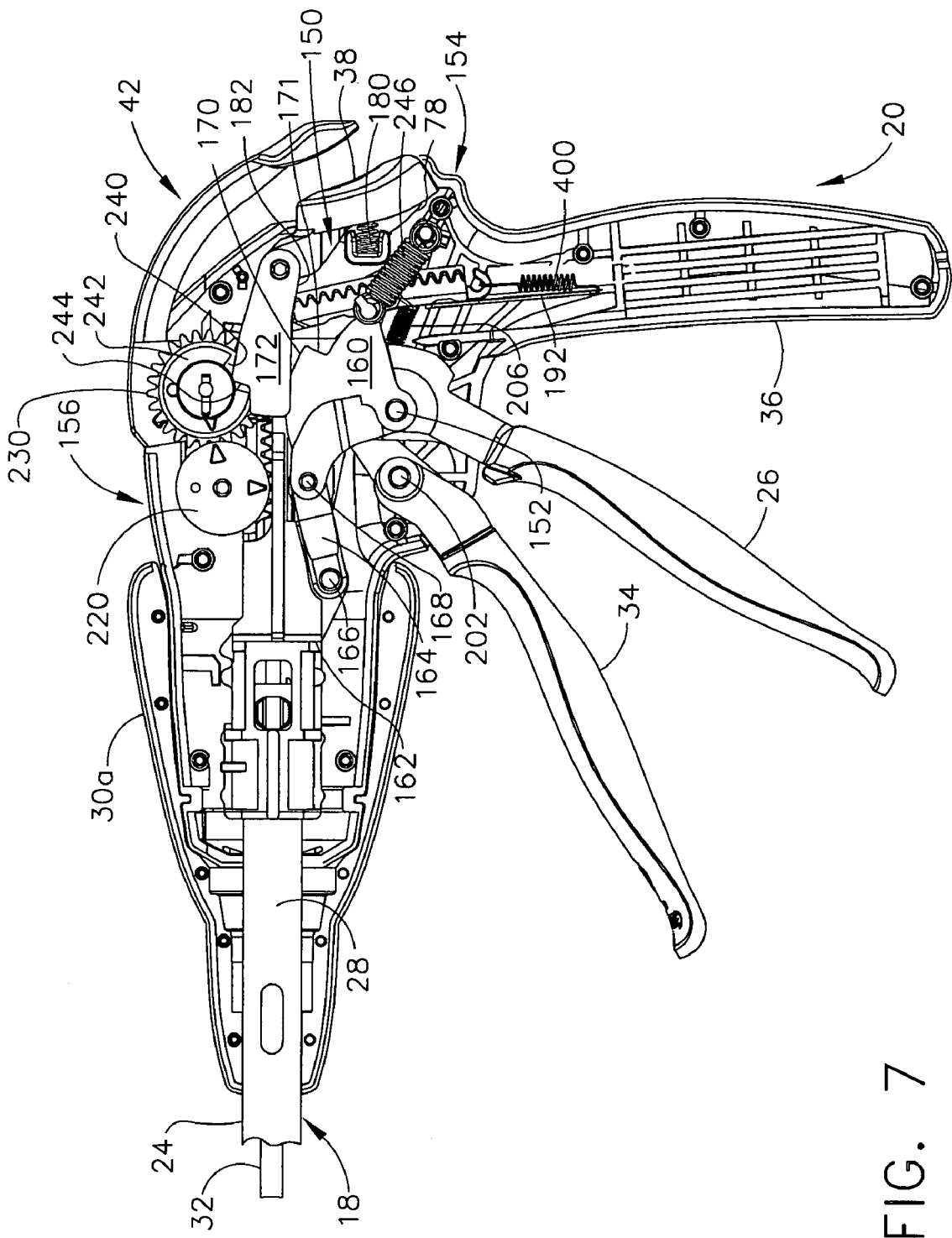
FIG. 7 is a left side elevation view of the handle of the surgical stapling and severing instrument of FIG. 1 with a left housing shell removed.
Figure 8:
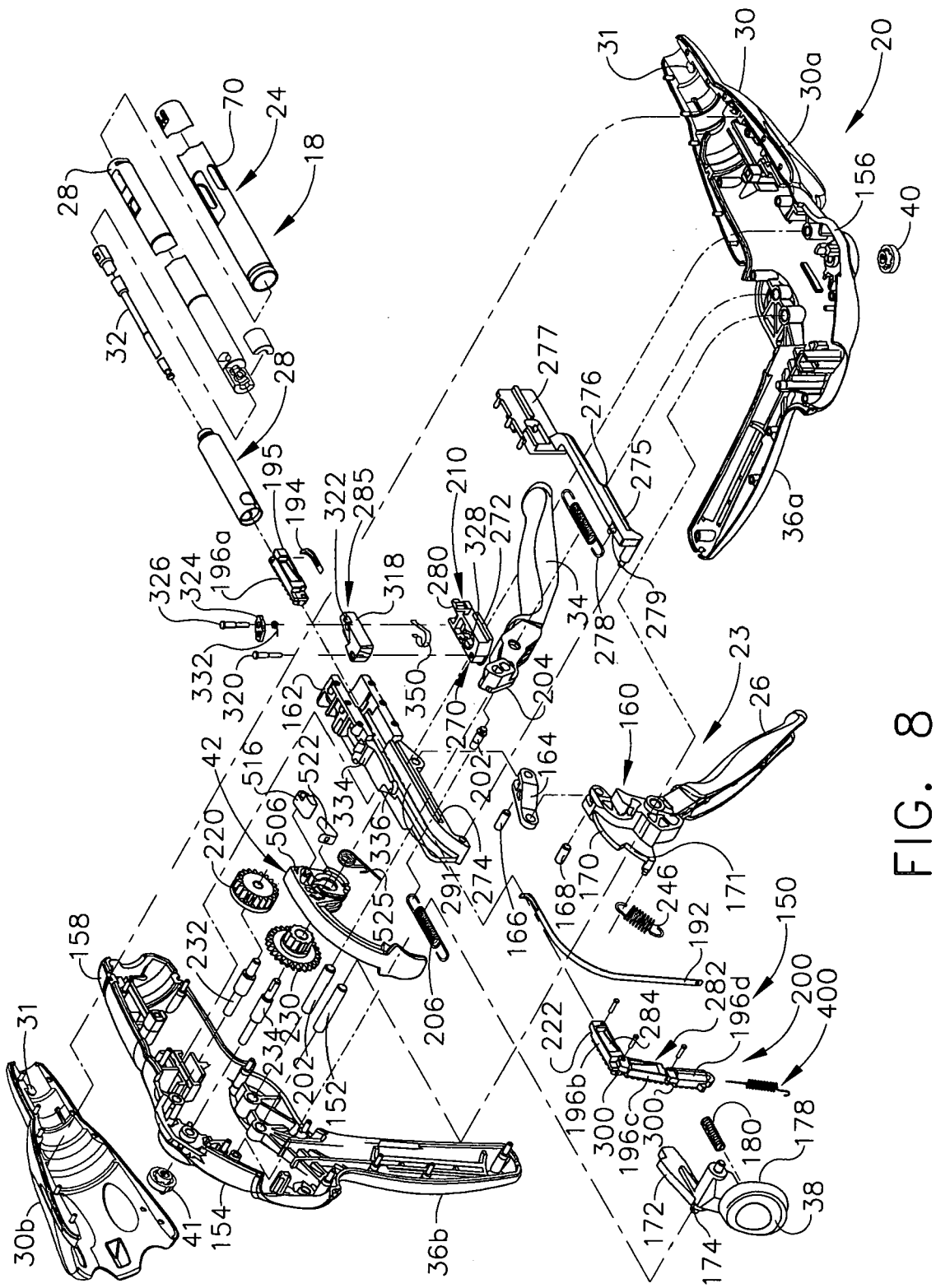
FIG. 8 is a perspective, exploded view of the handle of FIG. 7.
Figure 9:
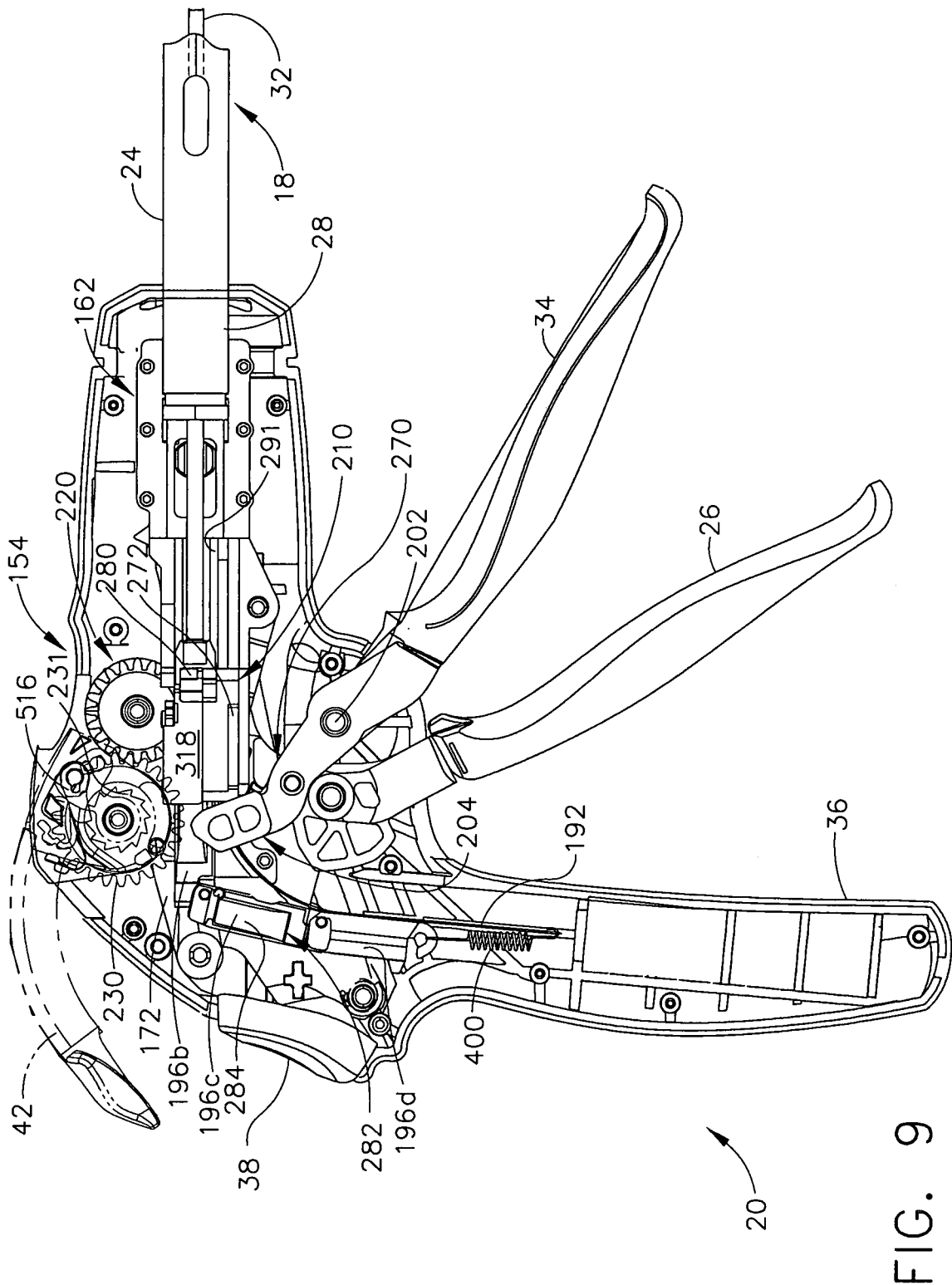
FIG. 9 is a right side elevational view of the handle of the surgical stapling and severing instrument of FIG. 1 with a right handle shell portion removed and with the closure trigger in the unlocked position.

With reference to FIGS. 7-9, the elongate shaft assembly 18 has as its outer structure a longitudinally reciprocating closure tube 24 that pivots the anvil 14 (FIGS. 1 and 2) to effect closure in response to proximal depression of the closure trigger 26 of the handle assembly 20. The elongate channel 18 is connected to the handle assembly 20 by a frame 28 that is internal to the closure tube 24. The frame 28 is rotatably engaged to the handle assembly 20 so that twisting the rotation knob 30 causes rotation of the implement portion 22. With particular reference to FIG. 8, each half shell 30a, 30b of the rotation knob 30 includes an inward projection 31 that enters a respective longer side opening 70 in the closure tube 24 and inward to engage the frame 28 that determines the rotated position of the implement portion 22. The longitudinal length of the longer opening 70 is sufficiently long enough to facilitate longitudinal movement of the closure tube 24 during the closure operation.

Closure System

In various embodiments, operation of the closure tube 24 is controlled by means of a closure drive 23 which includes the closure trigger 26. The closure trigger 26 has a an upper portion 160 that is configured to activate a closure yoke 162 via a closure link 164. The closure link 164 is pivotally attached at its distal end to the closure yoke 162 by a closure yoke pin 166 and is pivotally attached to the closure trigger 26 at its proximal end by a closure link pin 168. As can be seen in FIG. 7, the closure trigger 26 is urged to the open position by a closure trigger tension spring 246 that is connected proximally to the upper portion 160 of the closure trigger 26 and a handle housing 154 formed by right and left half shells 156, 158.

The upper portion 160 of the closure trigger 26 also includes a proximal crest 170 that has an aft notch 171 formed therein. See FIGS. 7 and 8. In various embodiments, a closure release button 38 is pivotally attached to the handle housing 154 by a pivot rod arrangement 174. As can be seen in FIG. 8, a locking arm 172 protrudes from the closure release button 38 and, as will be discussed in further detail below, is configured to lockingly engage the upper portion 160 of the closure trigger 26. A compression spring 180 is employed between the closure release button 38 and the handle housing 154 to bias the closure release button away from the housing 154 about the pivot rod assembly 174. FIG. 7 depicts the closure trigger 26 in an unactuated position. As can be seen in that Figure, when in that position, the pivoting locking arm 172 rides upon the proximal crest 170. Such action of the locking arm 172 causes the closure release button 38 to be drawn in towards the handle housing 154 against the force of coil spring 180. When the closure trigger 26 reaches its fully depressed position, the pivoting locking arm 172 drops into the aft notch 171 in the upper portion of the locking trigger 26 under the urging of the compression spring 180. When in that position, the closure trigger is locked in position. In addition, as will be further discussed below, when the locking arm 172 is in that locked position, the firing trigger 34 may be actuated to actuate the firing mechanism 150. When the firing mechanism 150 is in the retracted position, manual depression of the closure release button 38 rotates the pivoting locking arm 172 upward out of retaining engagement with the aft notch 171 in the upper portion of the closure trigger 26 and thereby unlocks the closure trigger 26.

Firing System

In various embodiments of the invention, a linked transmission firing drive 150 of the type disclosed in U.S. Pat. No. 7,083,075 to Jeffrey S. Swayze, Frederick E. Shelton, IV, Kevin R. Doll, and Douglas B. Hoffman, entitled Multi-Stroke Mechanism With Automatic End of Stroke Retraction, issued Aug. 1, 2006, the relevant portions of which are herein incorporated by reference, may be employed to extend and retract the firing rod 32 as will be further discussed below. With the closure trigger 26 retracted and fully depressed, the firing trigger 34 is unlocked and may be depressed toward the pistol grip 36 multiple times to effect the firing of the end effector 12. As depicted in FIG. 8, the firing trigger 34 pivots about a firing trigger pin 202 that laterally traverses and is attached to the right and left half shells 156, 158.

An upper portion 204 of the firing trigger 34 moves distally about the firing trigger pin 202 as the firing trigger 34 is depressed toward the pistol grip 36, stretching a proximally placed firing trigger tension spring 206 connected between an upper portion 204 of the firing trigger 34 and the housing 154. See FIGS. 7 and 8. The upper portion 204 of the firing trigger 34 engages a firing mechanism 150 in the form of a linked rack 200 during each firing stroke depression by a spring biased side pawl mechanism 210 that also disengages when the firing trigger 34 is released.

Linked Rack

Figure 10:
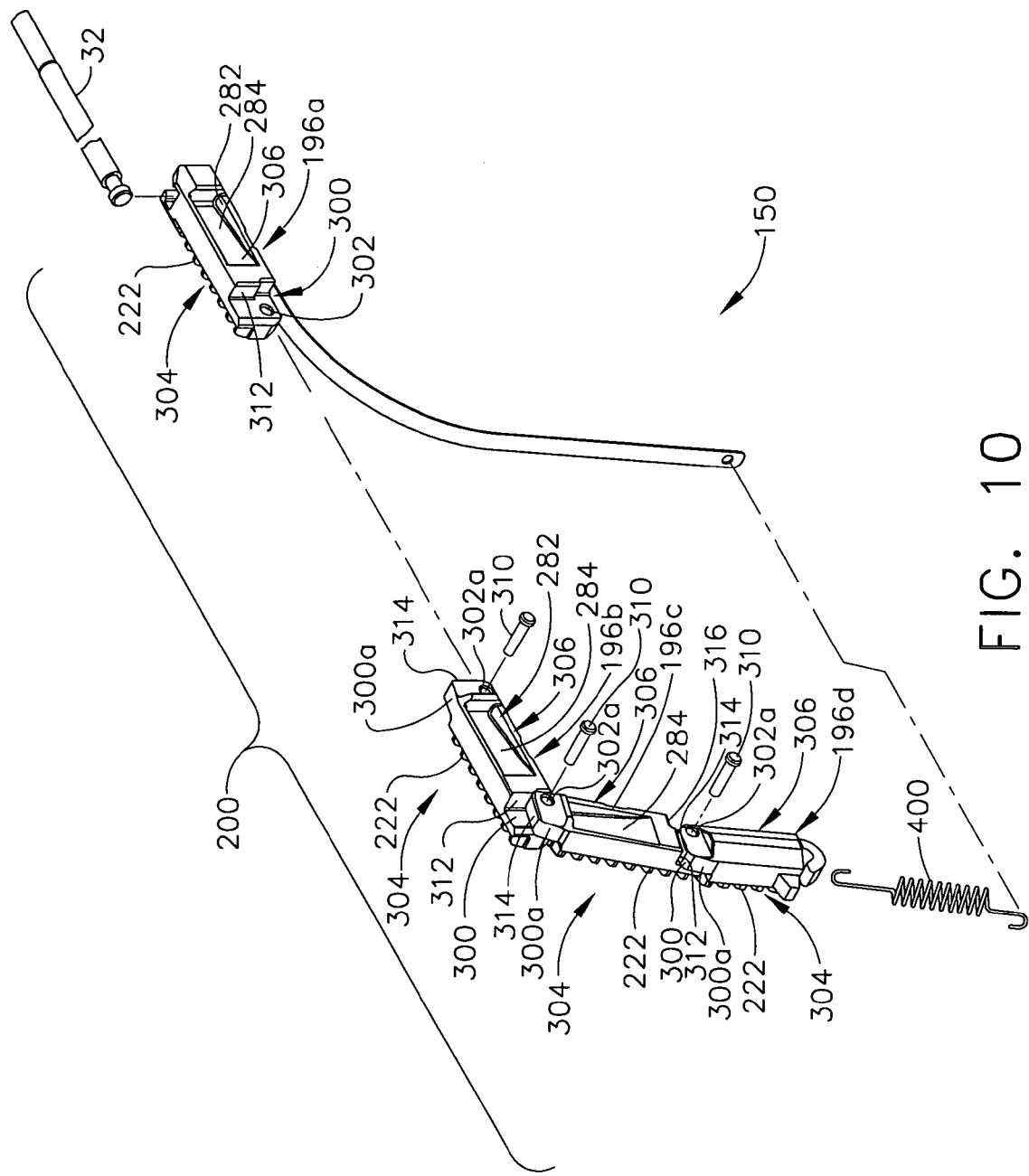
FIG. 10 is a right side exploded assembly view of the linked rack of the firing mechanism of FIG. 9.

As can be seen in FIGS. 8 and 10, each link 196a-d is pinned to adjacent links 196a-d for downward, proximal rotation into the pistol grip 36. Although bendable in this direction, the linked rack 200 forms a rigid configuration when against a columnar loading, especially a loading that would otherwise urge the distal links 196a-d to bend upwardly. In particular, each link 196a-c proximally terminates in an extension 300 having lateral through hole 302 on a lower portion thereof; Similarly, each link 196b-d distally terminates in an extension 300a that has a lateral hole 302a therethrough. As can be seen in FIG. 10, the holes 300, 300a are aligned to receive corresponding pivot pins 310 therethrough to hingedly attach the links 196a-d together in a linear fashion.

Each leading link 196a-d has a flat surface 312 at the proximal end that is generally perpendicular to the direction of columnar loading from the firing rod 32. Each trailing link 196a-d has a contact surface 314 at the distal end that is also generally perpendicular to the direction of columnar loading. The lateral through hole 302 is spaced away sufficient so that a notch 316 is formed between lower portions of adjacent flat surface 312 and contact surface 314 to provide clearance for downward pivoting of the trailing link 196a-d relative to the leading link 196a-d. Yet, the upper portions of the adjacent flat surface 312 and contact surface 314 are registered for abutment as the leading and trailing links 196a-d are longitudinally aligned, thereby resisting further upward deflection.

When adjacent links 196a-d are horizontally aligned, the holes 302 and pins 310 are located below the line of action of the firing rod 32. As will be discussed in further detail below, when loads are applied to the firing trigger 34, a traction biasing mechanism 210 applies a pushing load along the line of action and biases consecutive horizontal links 196a-d together. Thus, imparting a line of action of a firing force above the pivot pins 310 maintains any leading links 196a-d in a rigid, straight configuration. It should be appreciated that although pinned connections between links 196a-d have been advantageously depicted, other resilient or flexible connection arrangements may be used. In addition, four links 196a-d are depicted, but various numbers and lengths of links may be selected depending on firing travel, radius of curvature, etc.

As can also be seen in FIG. 10, a left side 304 of each link 196a-d includes the toothed upper surface 222. In addition, a right side 306 of each link 196a-c has a ramped right-side track 282 formed by a proximally and rightwardly facing beveled surface 284. The distal end of the front link 196a is configured for attachment to the proximal end of the firing rod 32. As shown in FIG. 8, an arcuate band 192 may be employed to support the firing mechanism 150 as it is actuated. In various embodiments, the band is fabricated from steel or other metal. However, the band 192 may be successfully fabricated from other suitable materials. As can be seen in FIG. 8, a distally-disposed end 194 of the band 192 is attached to an attachment feature 195 on the front link 196a. In various embodiments, a small spring 400 may be coupled to the proximal end of the link 196d and the proximal end of the band 192 (FIGS. 8 and 9) to draw the links 196a-d into conforming engagement with the arcuate band 192. Those of ordinary skill in the art will understand that the links 196a-d and band 192 move essentially as a unit. Thus, spring 400 does not apply any retraction force whatsoever to the firing rod 32.

Side Pawl Mechanism

In various embodiments, the upper portion 204 of the firing trigger 34 engages the linked rack 200 during each firing trigger depression through a spring biased side pawl mechanism 210 that also disengages when the firing trigger 34 is released. In particular, a ramped right-side track 282 formed by a proximally and rightwardly facing beveled surface 284 in each of the links 1196a-1196d is engaged by a side pawl assembly 285 as the firing trigger 34 is depressed. Turning to FIG. 8, one form of a side pawl assembly 285 that may be successfully employed includes a pawl slide 270 that is configured with right and left lower guides 272. One guide 272 slides in a left track 274 formed in the closure yoke 162 below the rack channel 291 and the other guide 272 slides in a right track 275 in a closure yoke rail 276 that parallels rack channel 291. As can be seen in FIG. 8, the closure yoke rail 276 is attached to or is integral with a rack channel cover 277 that is coupled to the closure yoke 162 to enclose the rack channel 291. A compression spring 278 is attached between a hook 279 on a top proximal position on the closure yoke rail 276 and a hook 280 on a distal right-side of the pawl slide 270, which keeps the pawl slide 270 drawn proximally into contact with the upper portion 204 of the firing trigger 34.

Figure 11:
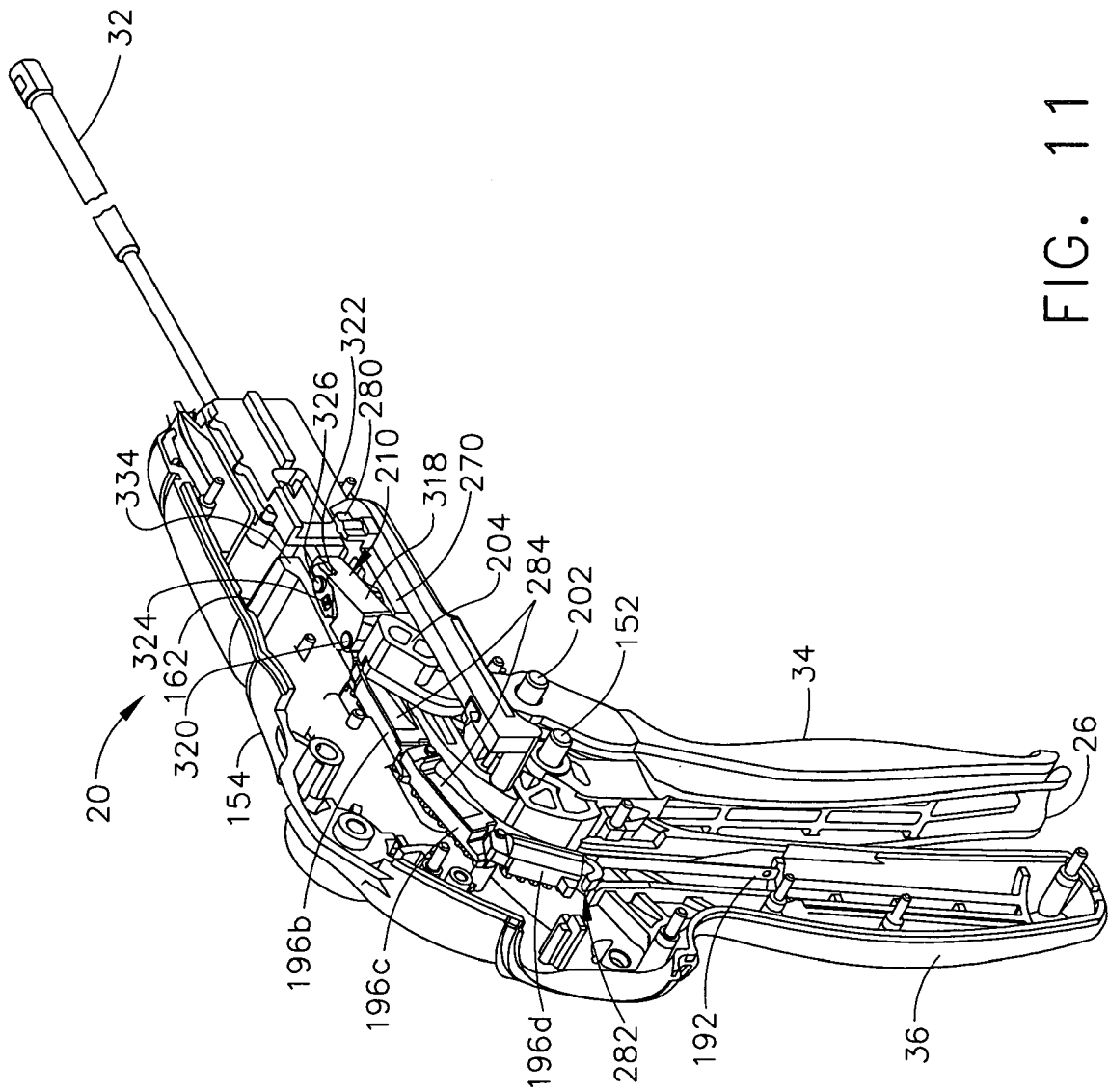
FIG. 11 is another right side elevational view of the handle of the surgical stapling and severing instrument of FIG. 1 with a right handle shell portion removed and with the closure trigger in the locked position.
Figure 12:
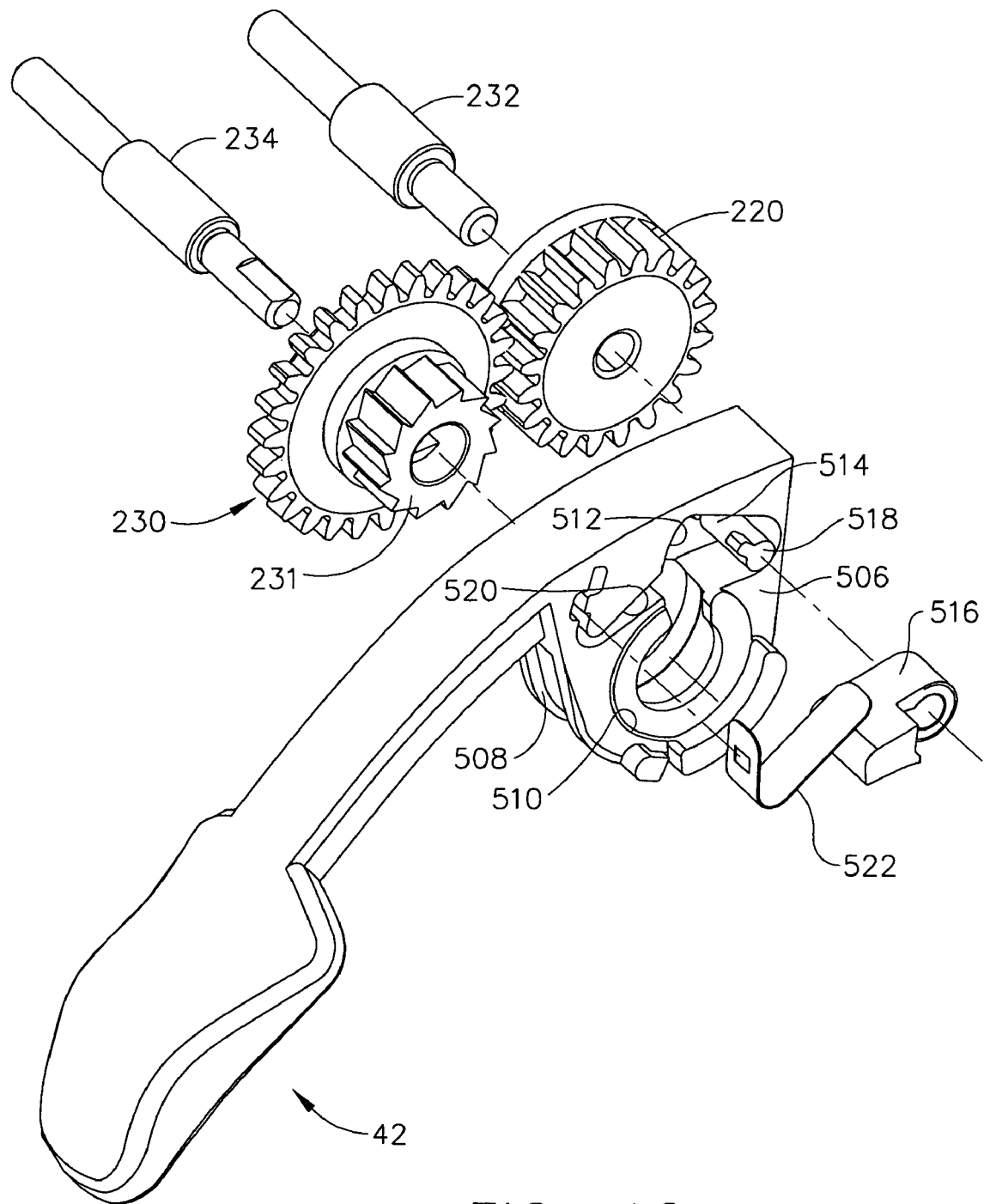
FIG. 12 is a right side exploded assembly view of a manual retraction assembly embodiment employed in the surgical stapling and severing instrument of FIG. 1.
Figure 13:
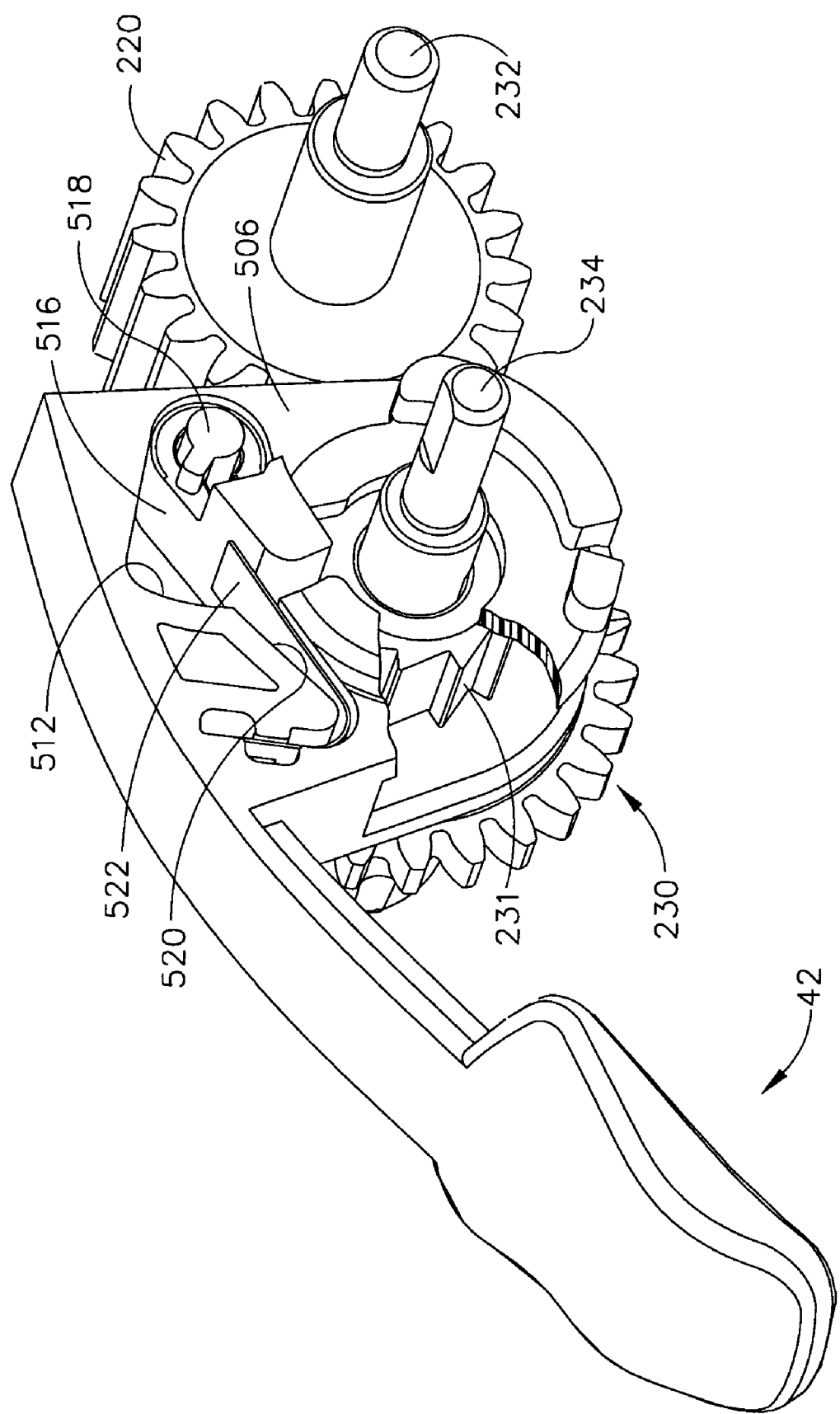
FIG. 13 is a right side perspective assembly view of the manual retraction assembly of FIG. 12.
Figure 14:
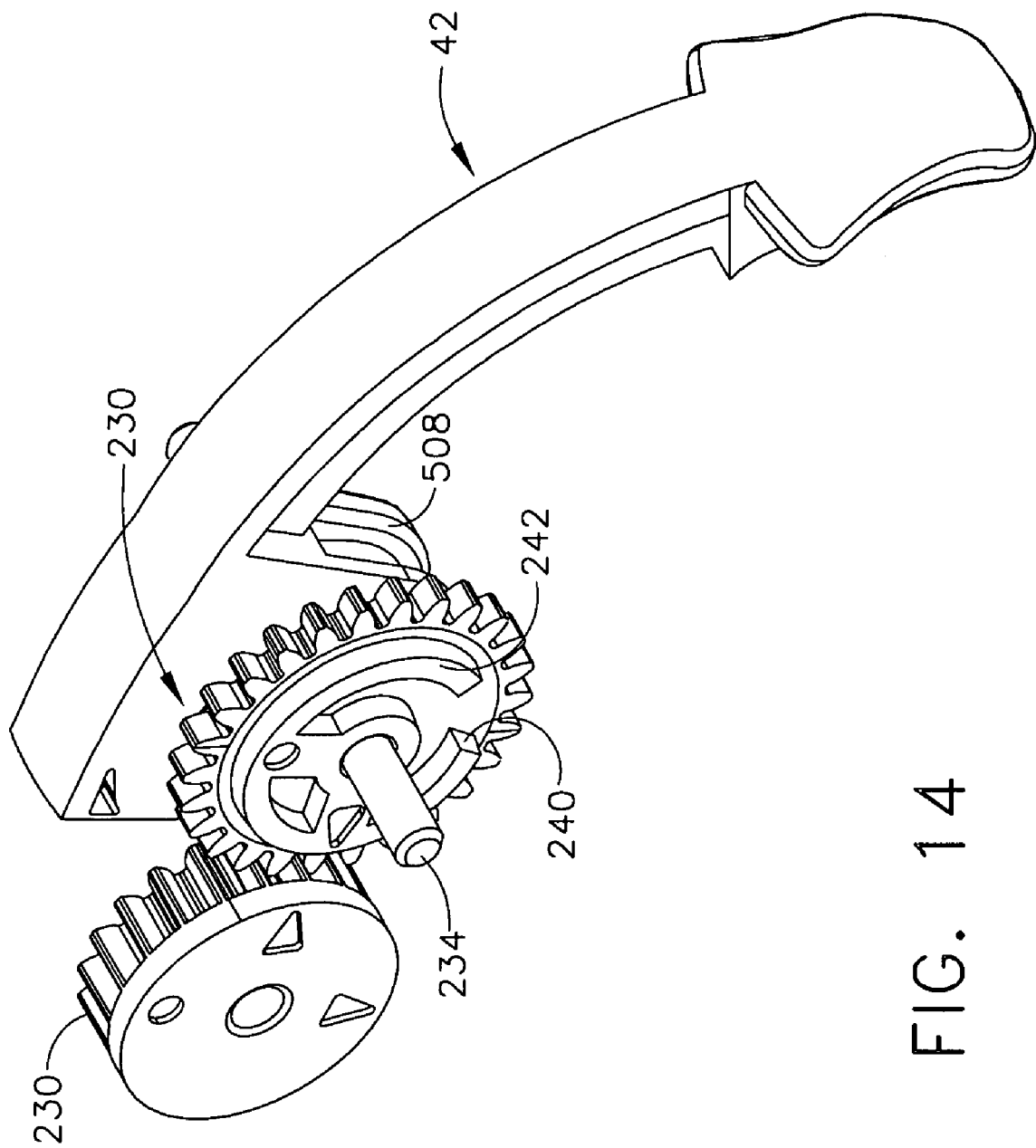
FIG. 14 is a left side assembly view of the manual retraction assembly of FIGS. 11 and 12.
Figure 15:
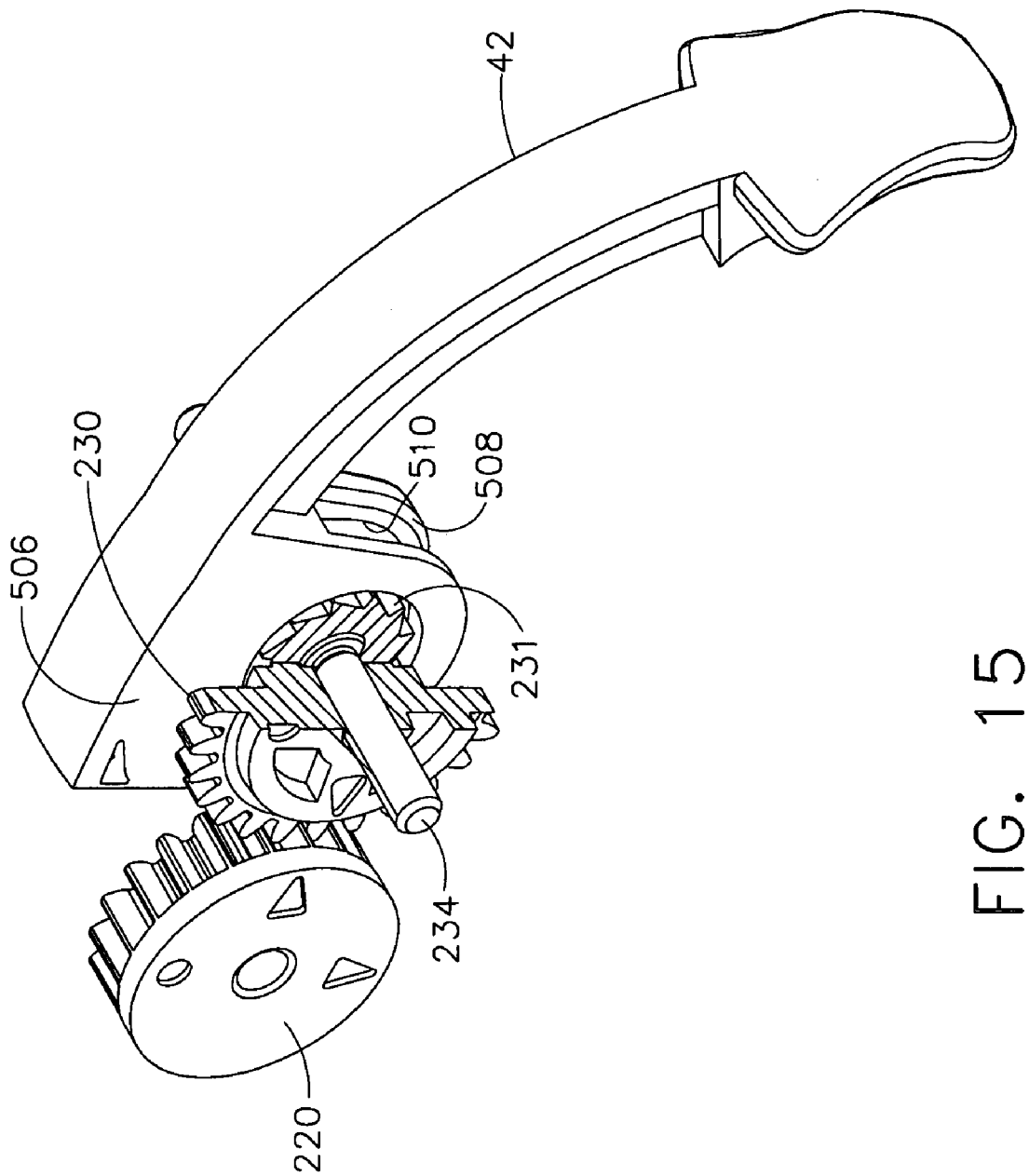
FIG. 15 is another left side assembly view of the manual retraction assembly of FIGS. 11-13 with the second gear shown in cross-section.

With reference to FIGS. 8 and 11, a pawl block 318 is located on the pawl slide 270 and is pivotally attached thereto by a vertical aft pin 320 that passes through a left proximal corner of pawl block 318 and pawl slide 270. A kick-out block recess 322 is formed on a distal portion of a top surface of the block 318 to receive a kick-out block 324 pivotally pinned thereto by a vertical pin 326 whose bottom tip extends into a pawl spring recess 328 on a top surface of the pawl slide 270. A pawl spring 330 (FIG. 8) in the pawl spring recess 328 extends to the right of the vertical front pin 326 urging the pawl block 318 to rotate counterclockwise when viewed from above into engagement with the ramped right-side track 282. A small coil spring 332 (FIG. 8) in the kick-out block recess 322 urges the kick-out block 324 to rotate clockwise when viewed from above, its proximal end urged into contact with a contoured lip 334 formed in the closure yoke 162 above the rack channel 291.

As the firing trigger 34 is fully depressed and begins to be released, the kick-out block 324 encounters a ridge 336 in the contoured lip 334 as the pawl slide 270 retracts, forcing the kick-out block 324 to rotate clockwise when viewed from above and thereby kicking out the pawl block 318 from engagement with the linked rack 200. The shape of the kick-out block recess 322 stops the clockwise rotation of the kick-out block 324 to a perpendicular orientation to the contoured lip 334 maintaining this disengagement during the full retraction and thereby eliminating a ratcheting noise.

Retraction System

The embodiment depicted in FIGS. 7-17 contains a retraction assembly 500 that is configured to enable the surgeon to manually retract the firing bar 32 without any other assistance from springs or other retraction arrangements that serve to place a drag on the firing system and which ultimately require the generation of higher firing forces to actuate the firing mechanism. As can be most particularly seen in FIGS. 16 and 17, in these embodiments, a first gear 220 is operably mounted to mesh with the toothed upper, left surfaces 222 of the linked rack 200. The first gear 220 also engages a second gear 230 that has a smaller right-side ratchet gear 231 thereon. Both the first gear 220 and second gear 230 are rotatably connected to the handle housing 154 respectively on front axle 232 and aft axle 234. One end of the axle 232 extends through the respective right housing half shell 156 and is attached to a right indication member in the form of an indicator gauge wheel 40. Similarly, the other end of the aft axle 232 extends through the left housing half shell 158 and is attached to a left indicator gauge wheel 41. Because the aft axle 234 is free spinning in the handle housing 154 and has a keyed engagement to the second gear 230, the indicator gauge wheels 40, 41 rotate with the second gear 230. The gear relationship between the linked rack 200, first gear 220 and second gear 230 may be advantageously selected so that the toothed upper surface 222 has tooth dimensions that are suitably strong and that the second gear 230 makes no more than one revolution during the full firing travel of the linked transmission firing mechanism 150.

Figure 16:
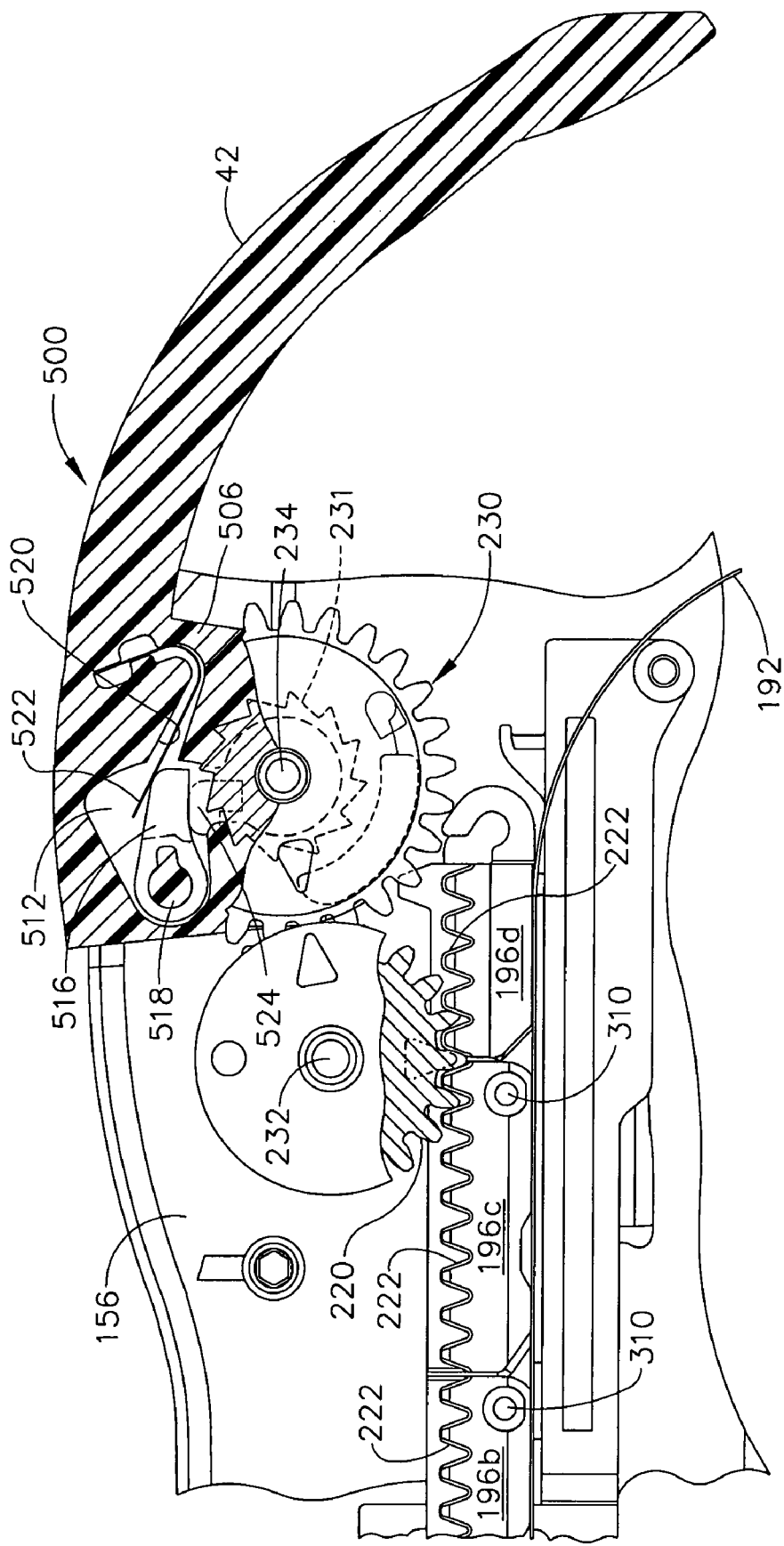
FIG. 16 is a left side elevational view of the manual retraction assembly and corresponding portion of the handle housing of FIGS. 12-15, with the manual retraction assembly shown in an up position and with portions of the assembly shown in cross-section for clarity.
Figure 17:
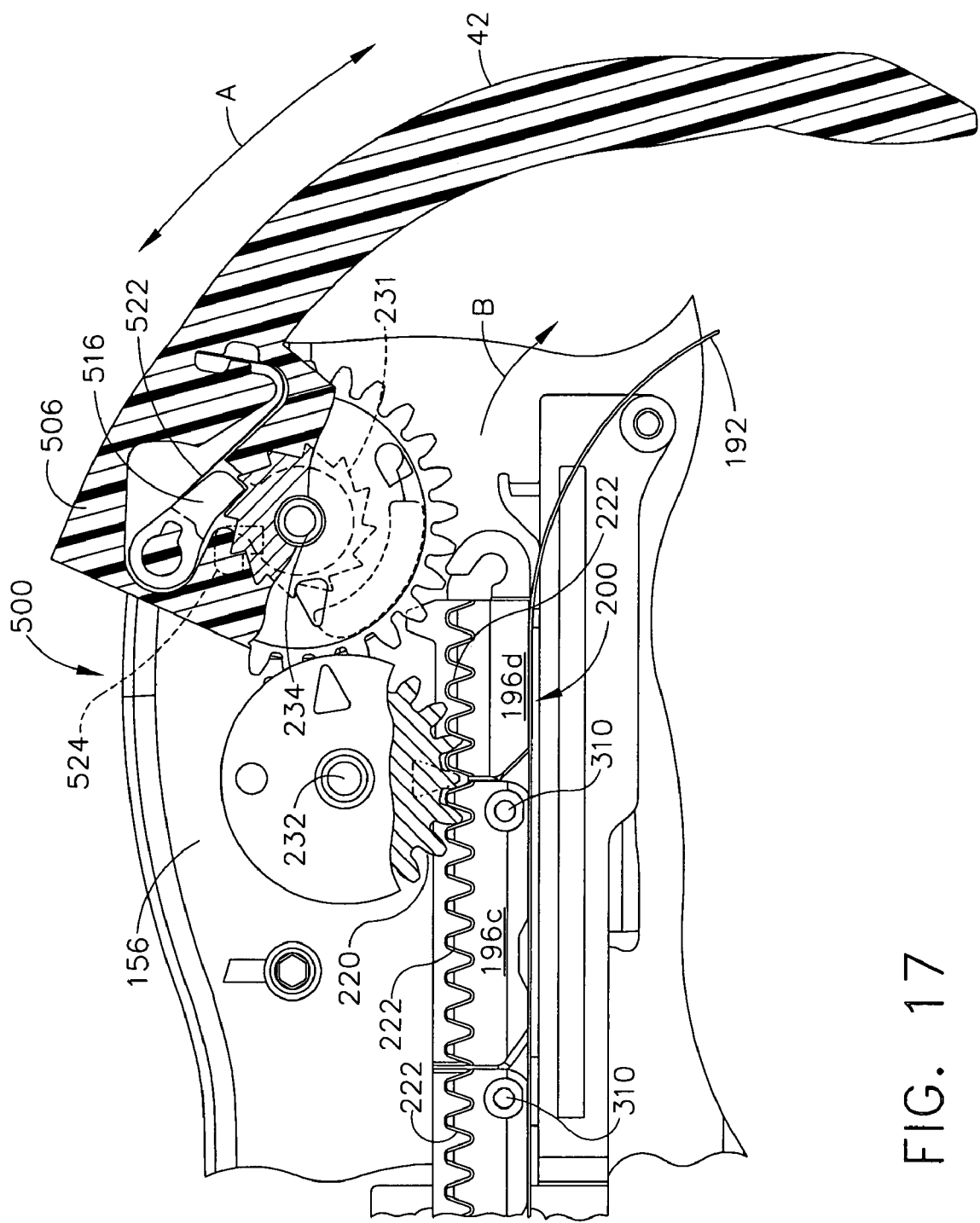
FIG. 17 is another left side elevational view of the manual retraction assembly and corresponding portion of the handle housing of FIGS. 12-16, with the manual retraction assembly shown in a down or actuated position and with portions of the assembly shown in cross-section for clarity.

The smaller right-side ratchet gear 231 of the second gear 230 extends into a hub 506 of a manual retraction member in the form of retraction lever 42 specifically aligned with a vertical longitudinally-aligned slot 508 (FIGS. 12 and 15) bisecting the hub 506. A lateral through hole 510 of the hub 506 communicates with an upper recess 512. See FIG. 12. A front portion 514 is shaped to receive a proximally directed retraction pawl 516 that pivots about a rightward lateral pin 518 formed in a distal end of the upper recess 512. An aft portion 520 is shaped to receive an L-shaped spring tab 522 that urges the retraction pawl 516 downward into engagement with the right-side smaller ratchet gear 231. A hold-up structure 524 (FIGS. 16 and 17) projects from the right half shell 156 into the upper recess 512 for supporting and preventing the retraction pawl 516 from engaging the smaller right-side ratchet gear 231 when the manual retraction lever 42 is up (FIG. 16). A spring 525 (FIG. 8) urges the manual retraction lever 42 into the up position.

After the firing sequence has been completed, the clinician can use the manual retraction lever 42 to retract the firing bar 32 to the unactuated position. This can be accomplished by grasping the pistol grip 36 and sequentially depressing and releasing the manual retraction lever 42. As the manual retraction lever 42 is depressed (FIG. 17), the locking pawl 516 rotates clockwise and no longer is held up by the hold-up structure 524 and engages the smaller right-side ratcheting gear 231, rotating the second gear 230 clockwise when viewed from the left. Because the second gear 230 is in meshing engagement with the forward idler gear 220, clockwise rotation of the second gear 230 causes the forward idler gear 220 to rotate in a counterclockwise direction. As the forward idler gear 220 rotates in a counterclockwise direction, it drives the linked rack in a proximal direction. Thus, continued ratcheting action (arrow A in FIG. 17) of the manual retraction lever 42 will cause the linked rack 200 to be retracted (arrow B) and draw the firing rod 32 to a fully retracted position.

In various embodiments, the invention may be constructed with means for providing the clinician with an indication of how far the firing bar 32 has been advanced and retracted. In those embodiments, the axle 234 on which the indicator gear 230 is journaled is connected to the externally viewable indicator wheels 40, 41. See FIG. 8. In such arrangement, the surgeon can determine the relative position of the firing mechanism 150 by observing the positions of the indicator wheels 40, 41 and thereby determine how many strokes of the firing trigger 34 are required to complete firing. For instance, full firing travel may require three full firing strokes and thus the indicator wheels 40, 41 rotate up to one-third of a revolution each per stroke. The gear relationship between the linked rack 200, first gear 220 and second gear 230 may be advantageously selected so that the toothed upper surface 222 has tooth dimensions that are suitably strong and that the second gear 230 makes no more than one revolution during the full firing travel of the linked transmission firing mechanism 150.

Interaction Between the Closure System and Firing System

When the linked rack 200 is fully retracted and both triggers 26, 34 are open as shown in FIGS. 7 and 9, an opening 240 in a circular ridge 242 on the left side of the second gear 230 is presented to an upper surface 244 of the locking arm 172. See FIG. 7. Locking arm 172 is biased into the opening 240 by contact with the closure trigger 26, which in turn is urged to the open position by a closure tension spring 246. As can be seen in FIG. 7,when a portion of the locking arm 172 extends into the opening 240 in the circular ridge 242, the second gear 230 cannot rotate. Thus, when the locking trigger 26 is in the unlocked position, the firing mechanism 150 cannot be actuated.

Figure 18:
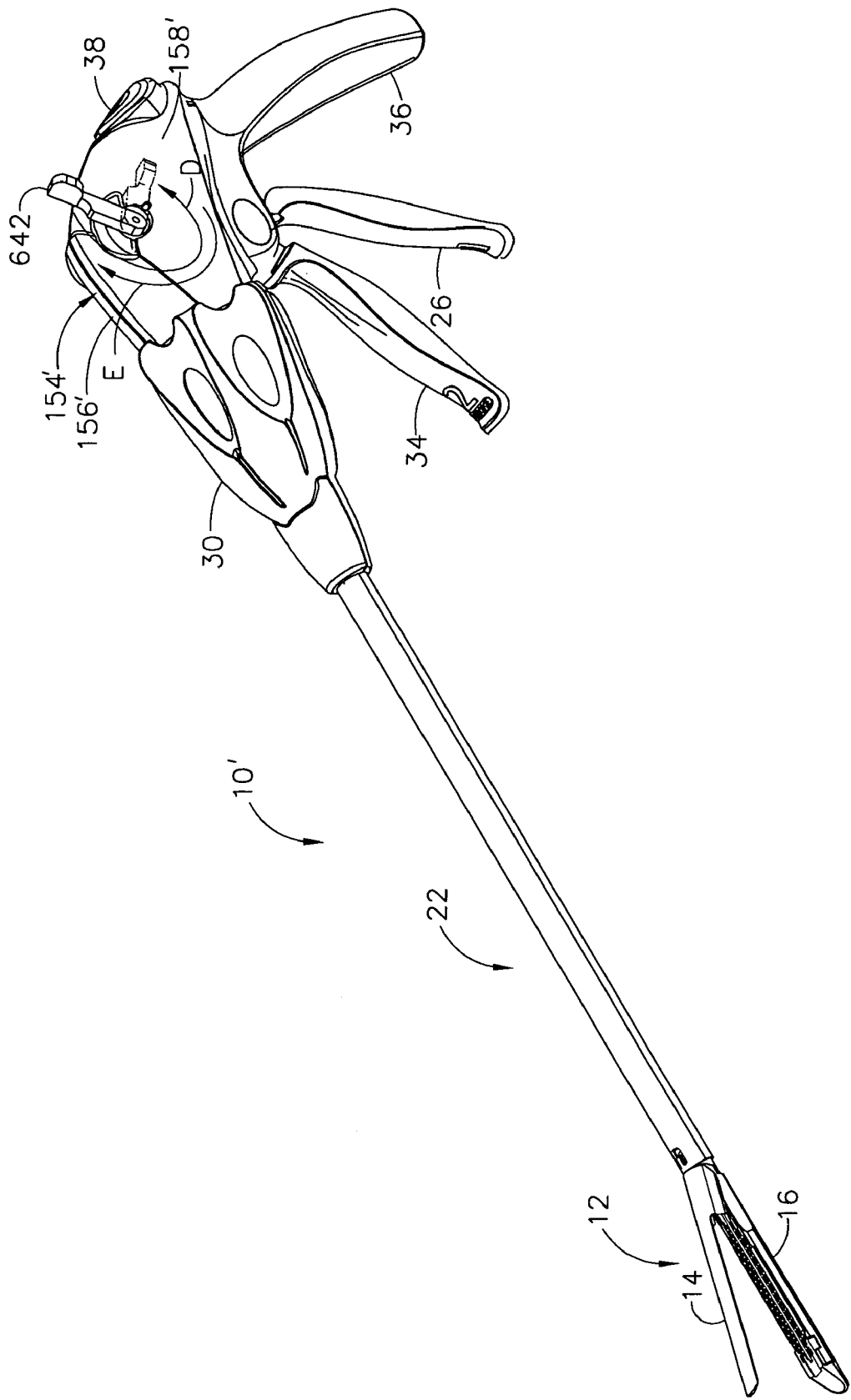
FIG. 18 is a perspective view of another surgical stapling and severing instrument of other various embodiments of the present invention.
Figure 19:
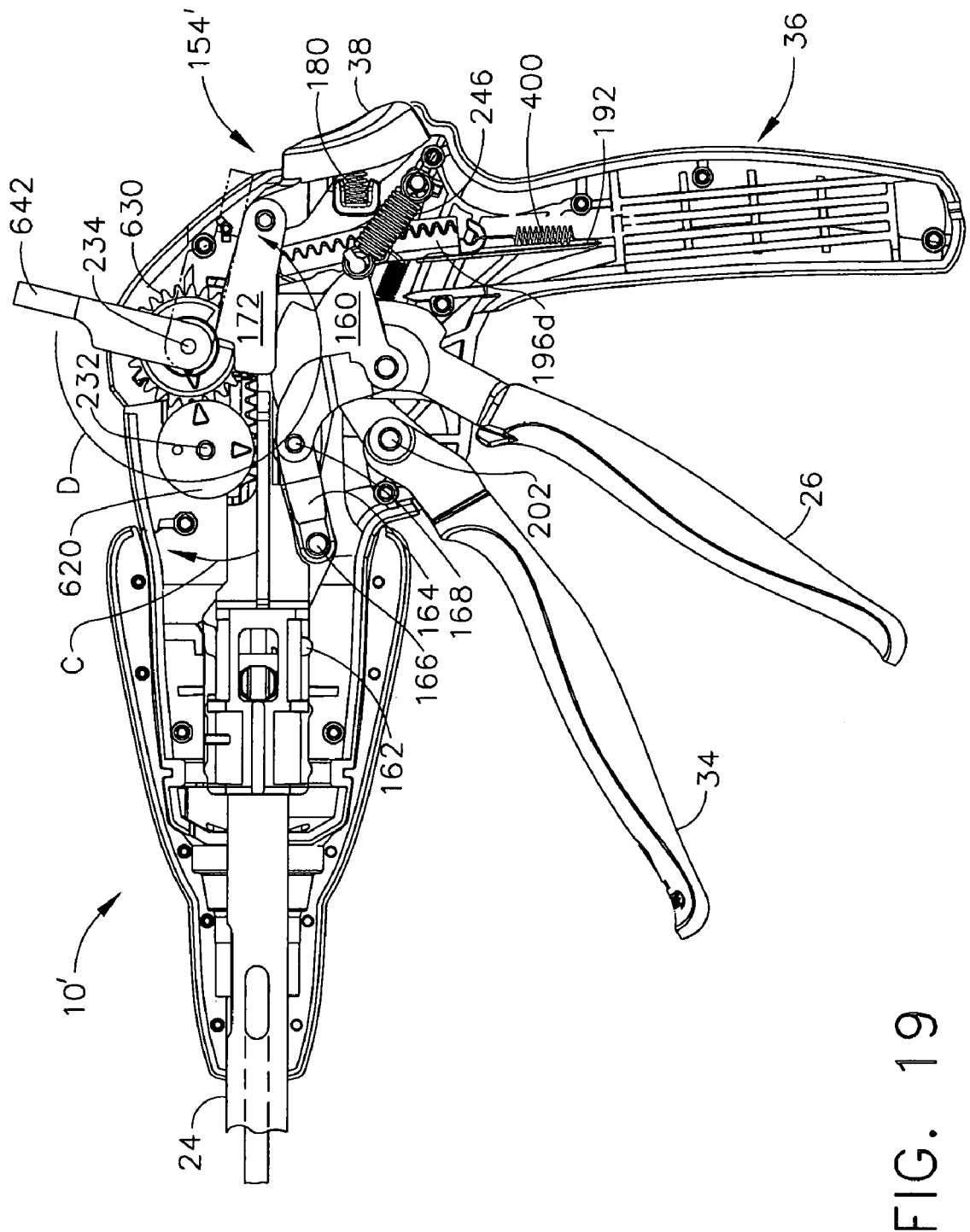
FIG. 19 is a left side elevation view of the handle of the surgical stapling and severing instrument of FIG. 18 with a left handle shell portion removed.
Figure 20:
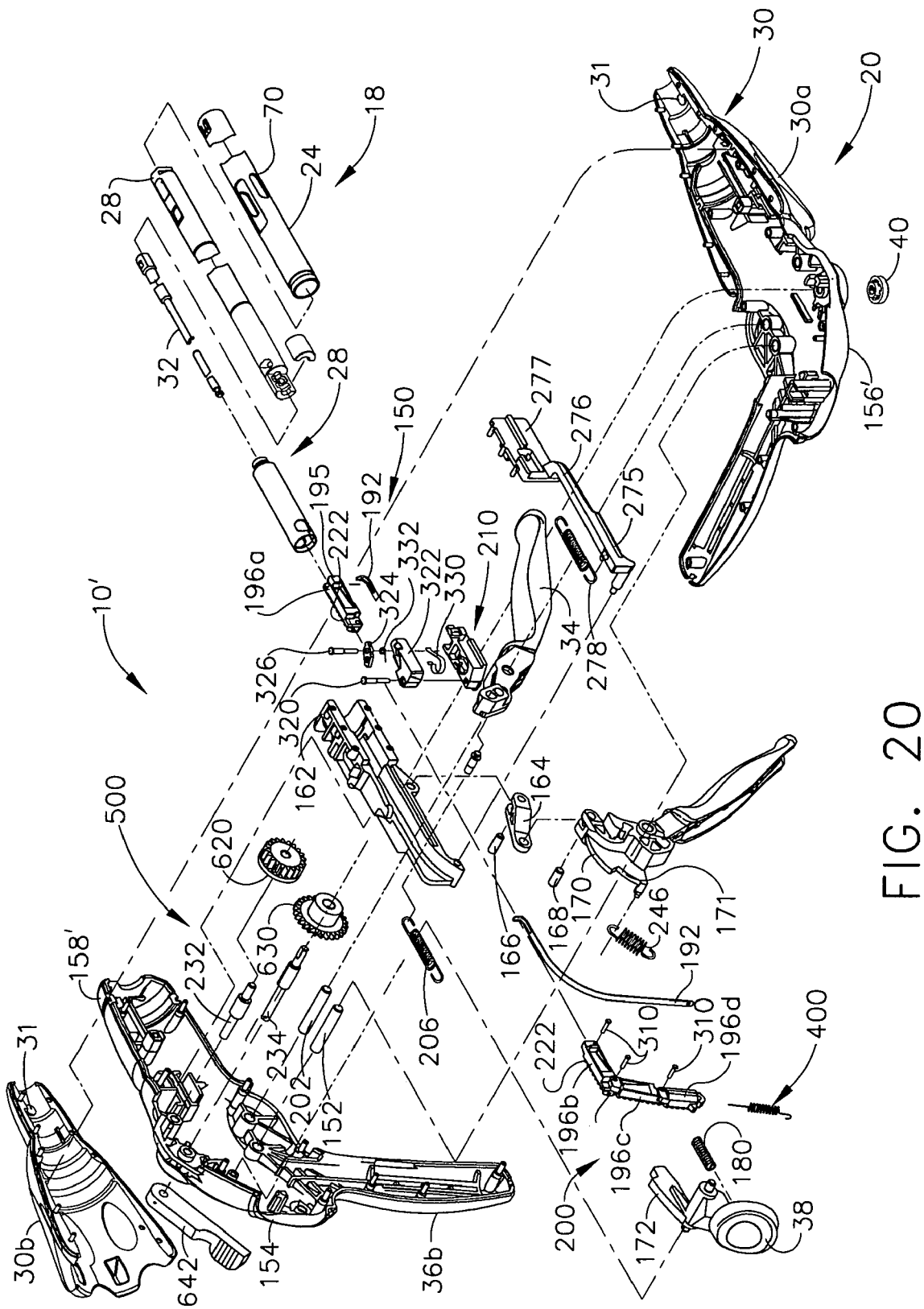
FIG. 20 is a perspective, exploded view of the handle of FIG. 19.
Figure 21:
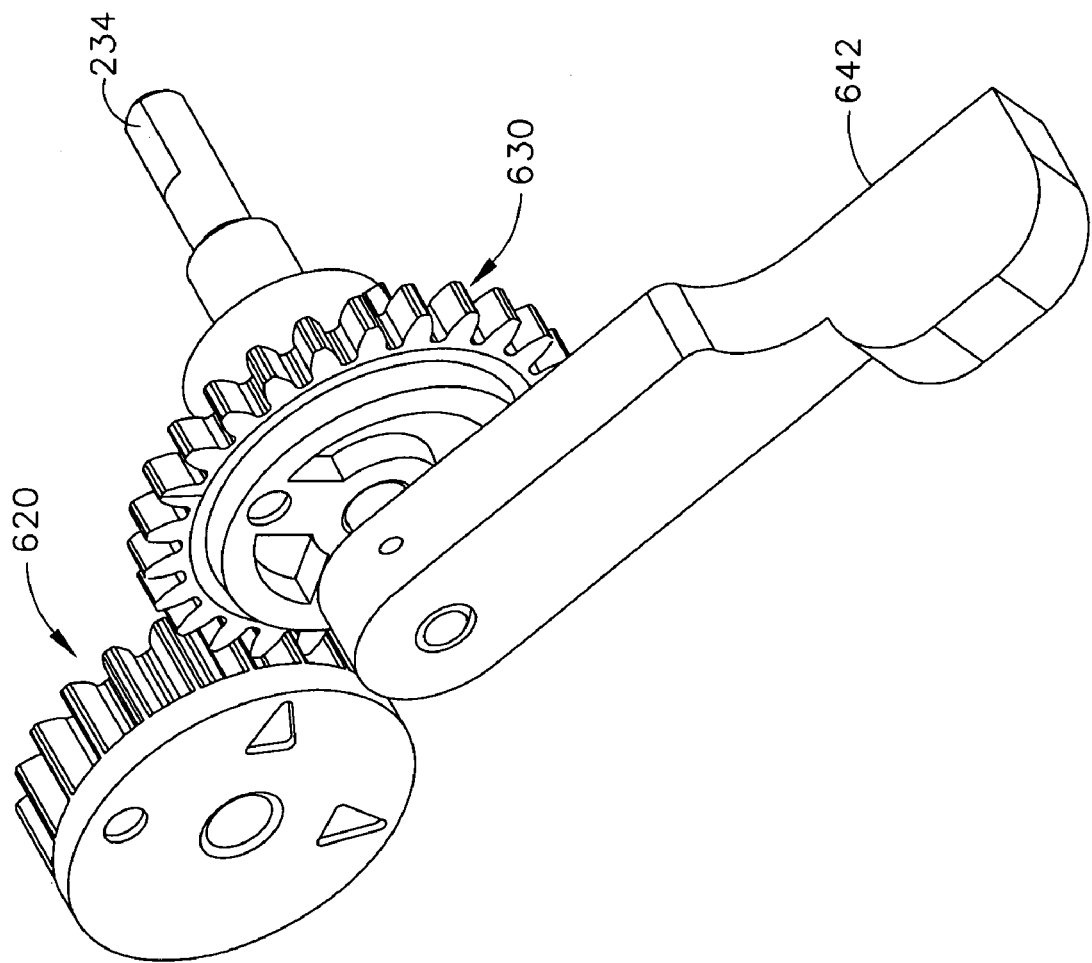
FIG. 21 is a left side assembly view of a manual retraction assembly of the surgical stapling and severing instrument of FIG. 18.
Figure 22:
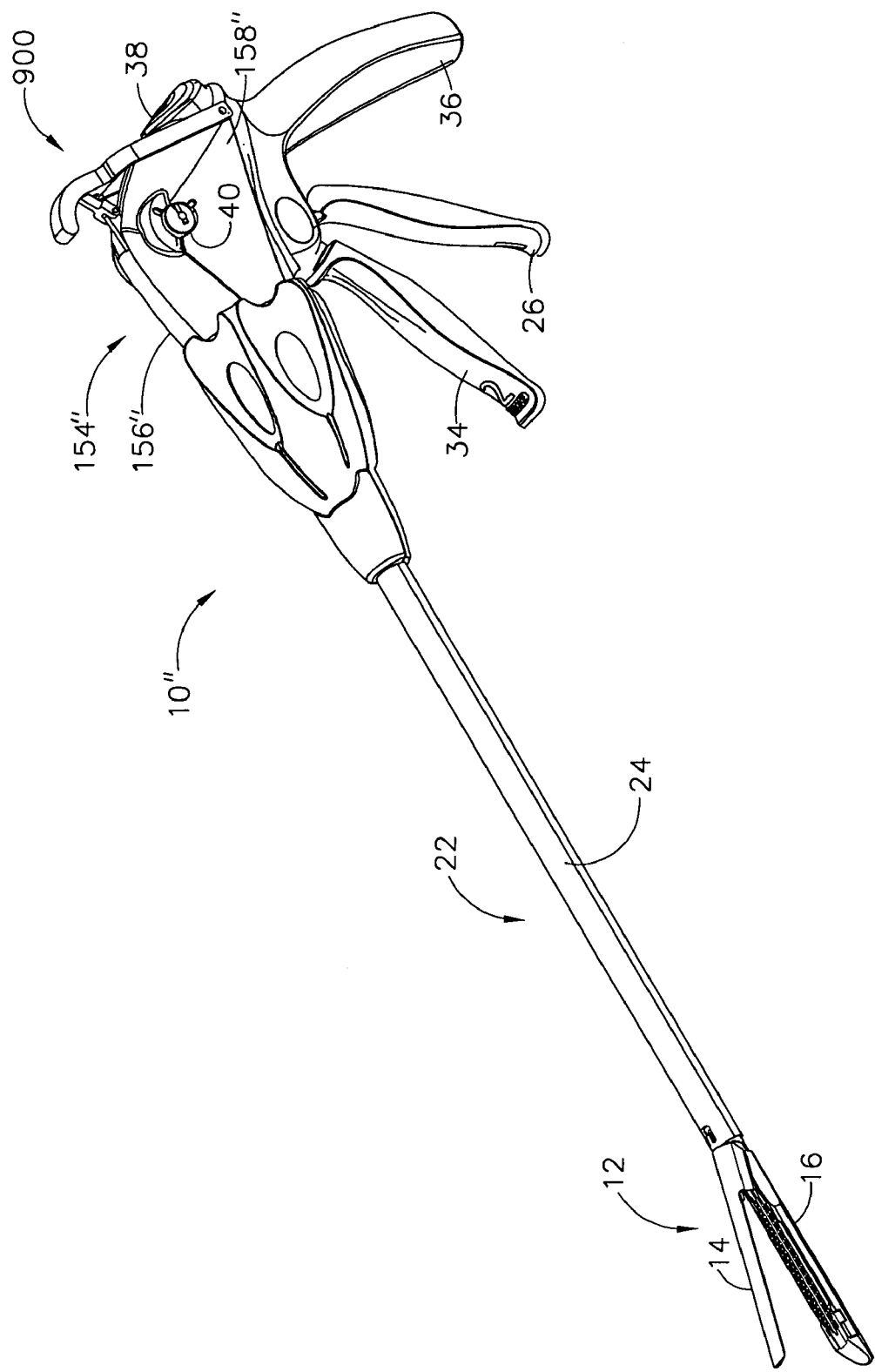
FIG. 22 is a perspective view of another surgical stapling and severing instrument of other various embodiments of the present invention.

FIGS. 18-21 illustrate another surgical stapling and severing instrument 10' of the present invention. As can be seen in FIG. 20, this embodiment may employ the same elements as the instrument 10 described above, except for the side mounted and rotatably supported manual retraction and indicating lever 642 and related components. More particularly and with reference to FIGS. 19 and 20, the instrument 10' includes a first gear 620 that is operably mounted to mesh with the toothed upper, left surfaces 222 of the linked rack 200. The first gear 620 also engages a hubbed aft gear 630. Both the first gear 620 and the aft gear 630 are rotatably connected to the handle housing 154' respectively on front idler axle 232 and aft idler axle 234. One end of the aft axle 232 extends through the respective right housing half shell 156' and is attached to a right indicator gauge wheel 40. The other end of the aft axle 232 extends through the left housing half shell 158' and is attached to the manual retraction indication lever 642. Because the aft axle 234 is free spinning in the handle housing 154' and has a keyed engagement to the second gear 630, the manual retraction and indication lever 642 rotates with the second gear 630.

As the clinician advances the firing rod 32 distally by ratcheting the firing handle 34 in the manner described in detail above, the toothed portions 222 of the links 196a-d cause the first gear 620 to rotate (direction "C" in FIG. 19) which, by virtue of its meshing engagement with the second gear 630, causes the second gear 630 and the manual retraction and indication lever 642 to rotate (direction "D" in FIG. 19). FIGS. 18 and 19 illustrate the position of the manual retraction and indication lever 642 in the unfired and fully fired positions. The gear relationship between the linked rack 200, first gear 620 and second gear 630 may be advantageously selected so that the toothed upper surface 222 has tooth dimensions that are suitably strong and that the second gear 630 makes no more than one revolution during the full firing travel of the linked transmission firing mechanism 150. Thus, the clinician can determine how far along the firing sequence is by monitoring the position of the manual retraction and indication lever 642.

After the firing sequence has been completed, the clinician can use the manual retraction lever 642 to retract the firing bar 32 to the unactuated (retracted) position. This can be accomplished by grasping the manual retraction lever 642 and rotating it in the clockwise (arrow "E" in FIG. 18). As the retraction lever 642 is rotated in that direction, it causes the second gear 630 to also rotate in that direction. Because the second gear 630 is in meshing engagement with the first gear 620, the first gear 620 rotates in a clockwise direction in FIG. 18 which draws the linked rack in the proximal direction until it reaches it starting-unfired position. Again, this embodiment does not employ any spring as or other retraction members that apply a retraction force to the firing system which must be overcome during the firing sequence. The gear relationship between the linked rack 200, first gear 620 and second gear 630 may be advantageously selected so that the toothed upper surface 222 has tooth dimensions that are suitably strong and that the second gear 630 makes no more than one revolution during the full firing travel of the linked transmission firing mechanism 150.

Figure 23:
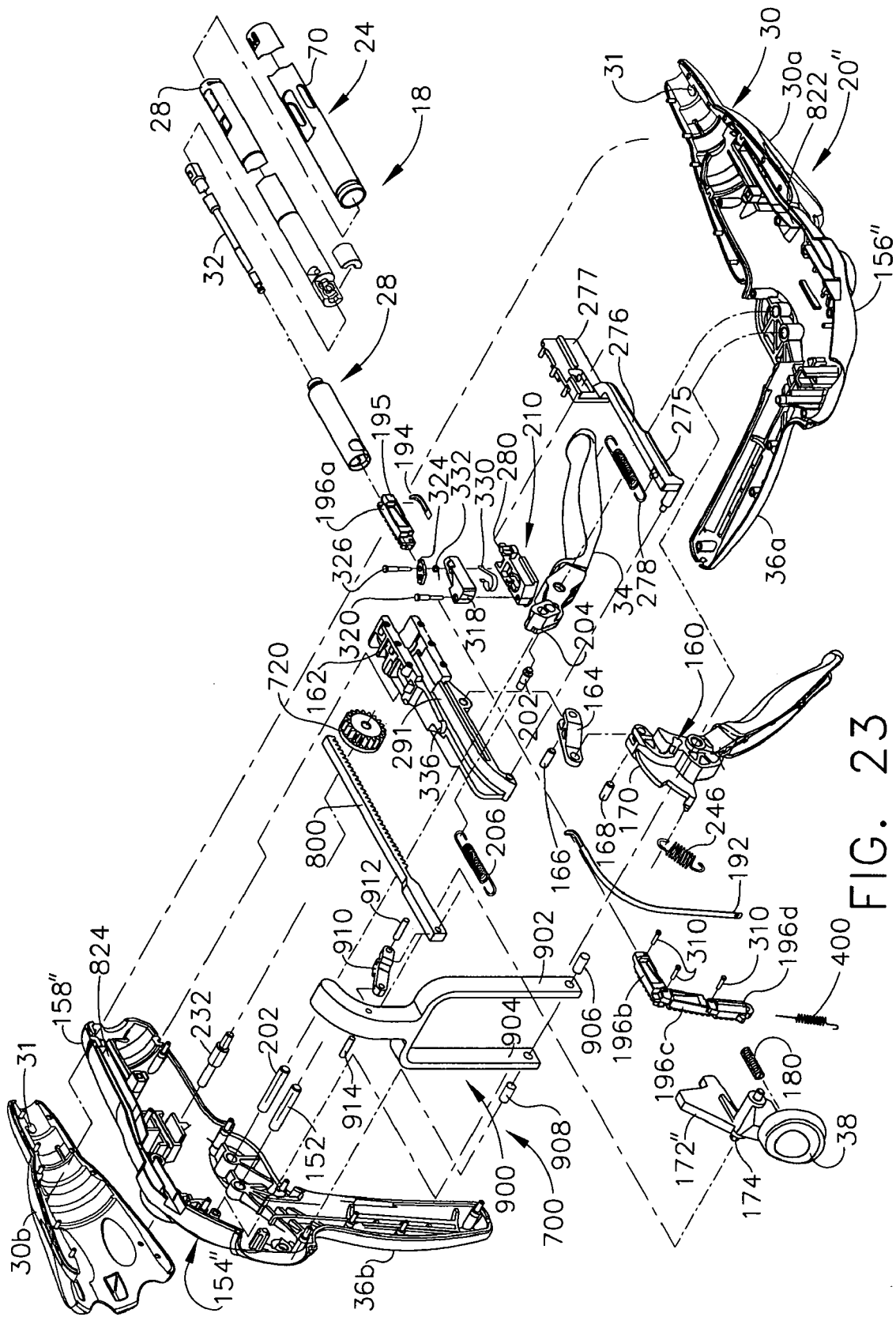
FIG. 23 is a perspective, exploded view of the handle of the surgical stapling and severing instrument of FIG. 22.

FIGS. 22-27 illustrate another surgical stapling and severing instrument 10" of the present invention. As can be seen in FIG. 23, this embodiment may employ many of the same elements as the instrument 10 described above. As can be most particularly seen in FIGS. 23-27, this embodiment employs a manual retraction assembly 700 for manually retracting the firing rod 32. In various embodiments, the manual retraction assembly 700 includes a drive gear 720 that is operably mounted to mesh with the toothed upper, left surfaces 222 of the linked rack 200. The drive gear 720 is rotatably supported within the handle housing 154" on an axle 232 that is supported between handle shell portions 156", 158". The manual retraction assembly 700 may further include a second gear rack 800 that is movably supported within a rack passage 820 formed in the handle housing 154". As can be seen in FIG. 23, a track portion 822 is formed in the right shell portion 156 and a track portion 824 is formed in the left shell portion 158. When the shell portions 156, 158 are interconnected together to form the handle housing 154", the track portions 822, 824 cooperate to form the rack passage 820. The rack passage 820 is sized relative to the second gear rack 800 such that the second gear rack 800 can move axially back and forth (arrow "F" in FIG. 26) within the handle housing 154". Second gear rack 800 is movably supported within the rack passage 820 and is in meshing engagement with the drive gear 720.

Figure 25:
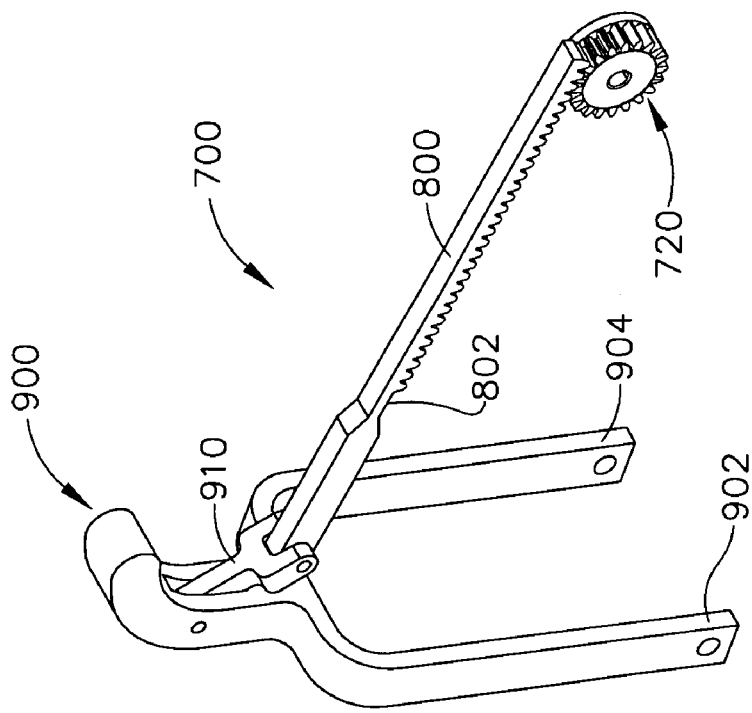
FIG. 25 is a perspective view of the manual retraction assembly of FIG. 24.
Figure 24:
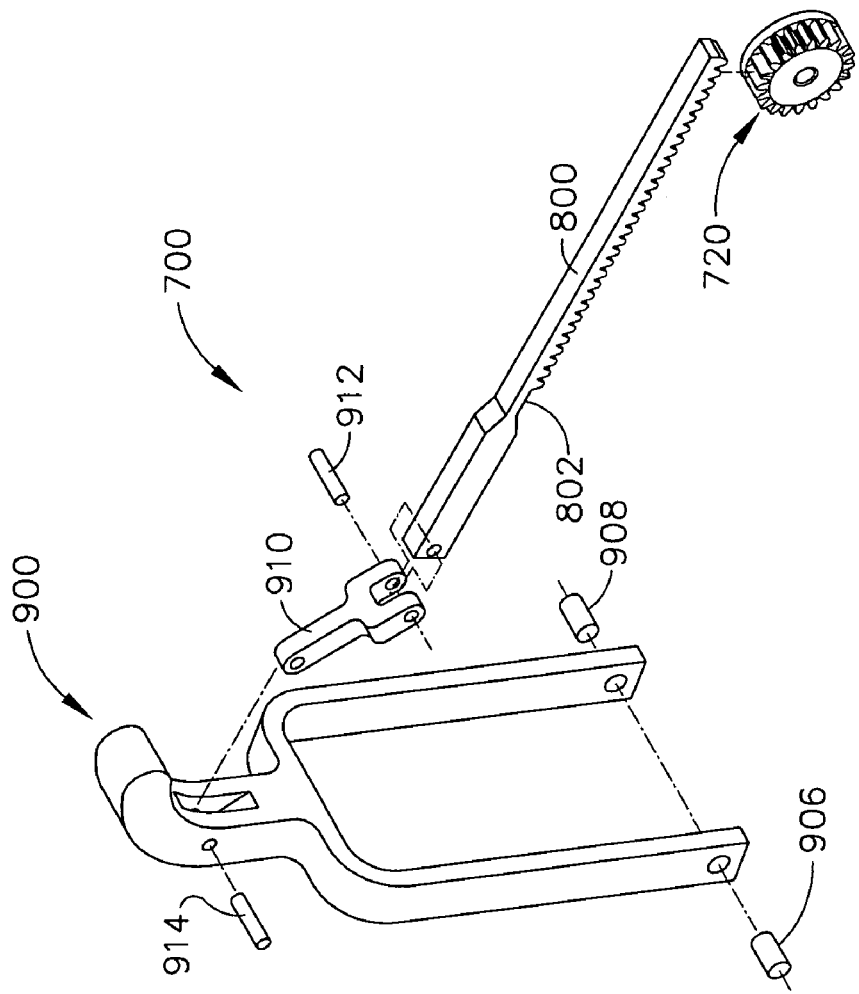
FIG. 24 is an exploded assembly view of a manual retraction assembly of the surgical stapling and severing instrument of FIG. 12.

As can be seen in FIGS. 24 and 25, the second gear rack 800 is attached to a retraction handle 900 by means of a handle yoke 910 that is pinned to the second gear rack 800 with a pin 912 and is also pinned to the retraction handle 900 by pin 914. The retraction handle 900 may be configured with a pair of pivot legs 902, 904 for pivotal attachment to the handle housing 154". In particular, leg 902 may be pinned to the right hand shell portion 156" by pin 906 and leg 904 may be pivotally pinned to left hand shell portion 158" by pin 908. See FIG. 23.

Figure 26:
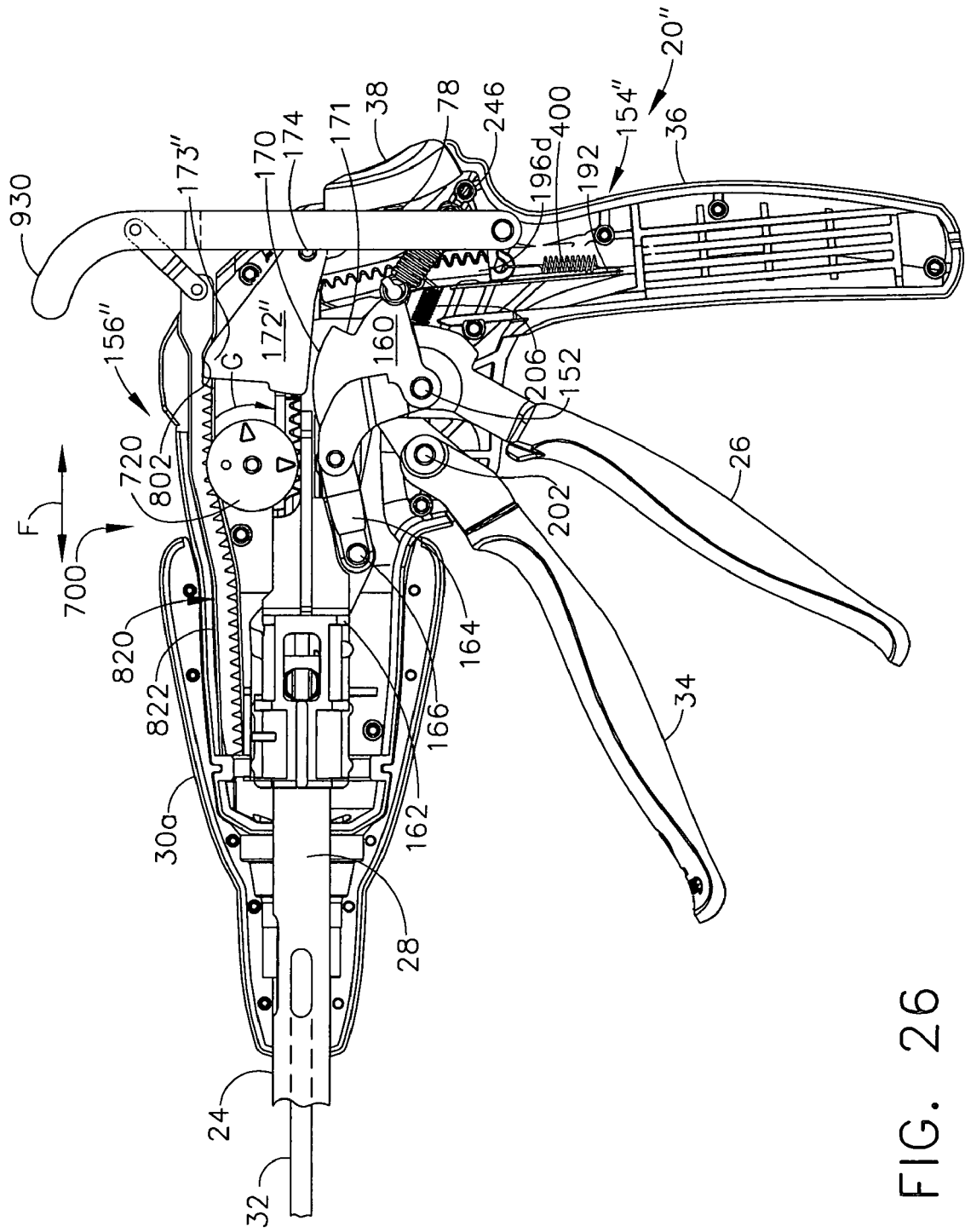
FIG. 26 is a left side elevation view of the handle of the surgical stapling and severing instrument of FIG. 22 with a left handle shell portion removed and the instrument in an unfired position.
Figure 27:
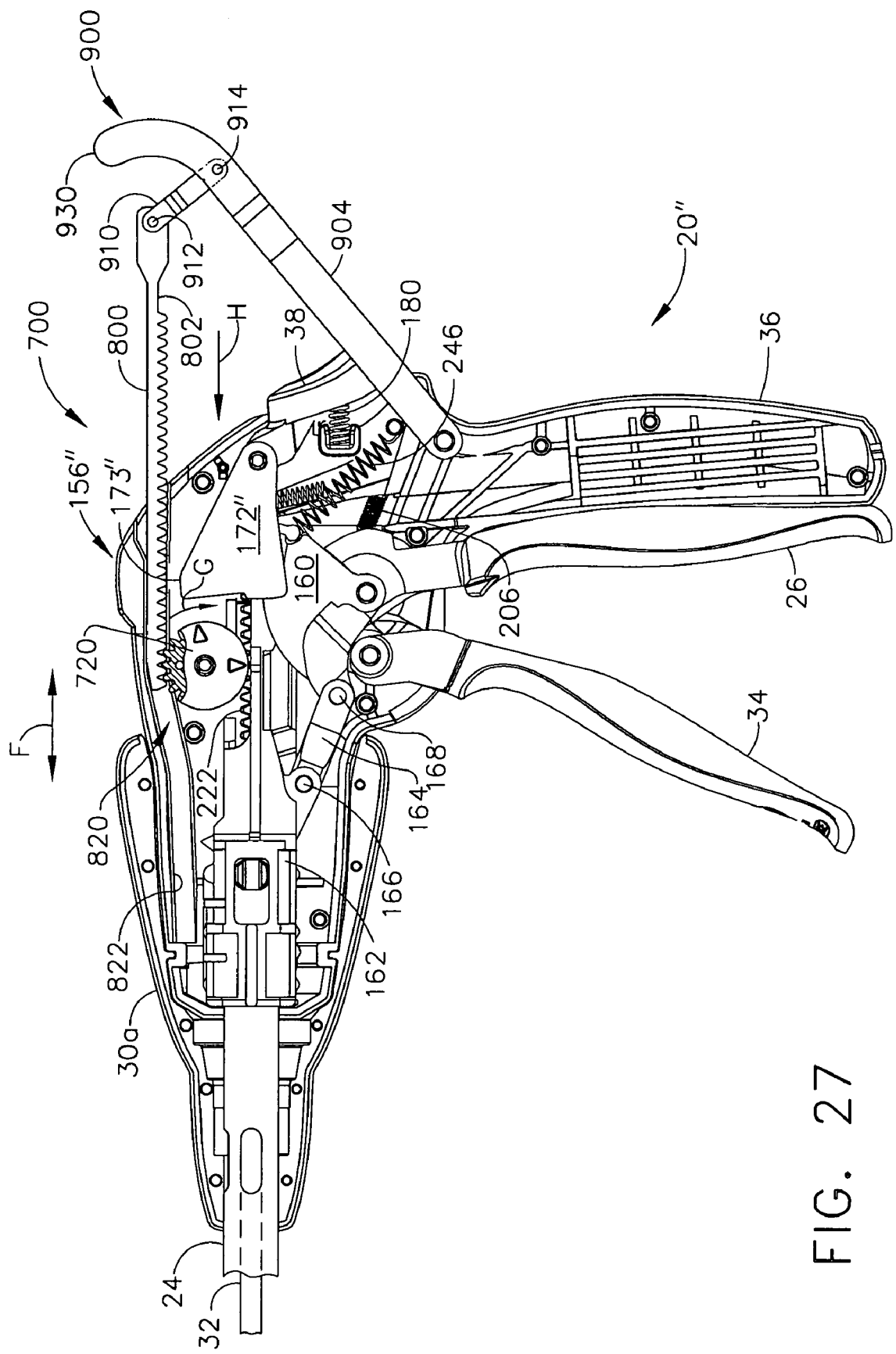
FIG. 27 is another left side elevational view of the handle of the surgical stapling and severing instrument of FIG. 22 with the left handle shell portion removed and with the closure trigger in the locked position and the manual retraction assembly in the fully retracted position.

As the clinician advances the firing rod 32 distally by ratcheting the firing trigger 34 in the manner described above, the toothed portions 222 of the links 196a-d cause the drive gear 720 to rotate clockwise (direction "G" in FIGS. 26 and 27) which, by virtue of its meshing engagement with the second gear rack 800, causes the second gear rack 800 to move in the proximal direction (arrow "H" in FIG. 27). FIG. 27 illustrates the position of the second gear rack 800 and the manual retraction handle 900 at the completion of the firing stroke (i.e., the position wherein the firing rod 32 has been moved to its distal most position). As can be seen in that Figure, a grip portion 930 of the retraction handle is spaced away from the handle housing 154. To retract the firing rod 32, the clinician simply pushes the retraction handle in the "H" direction until the second gear rack 800 reaches the position illustrated in FIG. 26 wherein the grip portion 930 is adjacent the handle housing 154. Those of ordinary skill in the art will appreciate that the clinician can monitor the progress of the firing stroke by observing the position of the retraction handle 900 as the clinician continues to ratchet the firing trigger 34. In addition, this embodiment does not employ any springs or other retraction members that apply a retraction force to the firing system which must be overcome during the firing sequence.

In various embodiments, the closure trigger 26 has a an upper portion 160 that is configured to activate a closure yoke 162 via a closure link 164. The closure link 164 is pivotally attached at its distal end by a closure yoke pin 166 to the closure yoke 162 and is pivotally attached at its proximal end by a closure link pin 168. As can be seen in FIG. 26, the closure trigger 26 is urged to the open position by a closure trigger tension spring 246 that is connected proximally to the upper portion 160 of the closure trigger 26 and a handle housing 154".

The upper portion 160 of the closure trigger 26 includes a proximal crest 170 with an aft notch 171. See FIGS. 23 and 26. The closure release button 38 and a pivoting locking arm 172" are connected by a central lateral pivot 174. A compression spring 180 biases the closure release button 38 proximally (clockwise about the central lateral pivot 174 as viewed from the right). With the upper portion 160 back when the closure trigger 26 is released as depicted in FIG. 26, the pivoting locking arm 172" rides upon the proximal crest 170 drawing in the closure release button 38. As can also be seen in FIG. 26, the upper end 173" of the pivoting locking arm 172" is configured to extend into a recess 802 in the second gear rack 800 to thereby prevent actuation of the gear rack 800 to fire the instrument 10". When the closure trigger 26 reaches its fully depressed position, it should be appreciated that the aft notch 171 is presented below the pivoting locking arm 172" which drops into and locks against the aft notch 171 under the urging of the compression spring 180. When the pivoting locking arm 172" drops out of engagement with the second gear rack 800, the gear rack 800 can then be axially advanced. With the firing components retracted, manual depression of the closure release button 38 rotates the pivoting locking arm 172" upward unclamping the closure trigger 26.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For instance, while a surgical stapling and severing instrument 10 is described herein that advantageously has separate and distinct closing and firing actuation, providing clinical flexibility. However, it should be appreciated that applications consistent with the present invention may include a handle that converts a single user actuation into a firing motion that closes and fires the instrument.

In addition, while a manually actuated handle is illustrated, a motorized or otherwise powered handle may benefit from incorporating a linked rack as described herein, allowing reduction of the size of the handle or other benefits. For instance, while partially stowing the linked rack into the pistol grip is convenient, it should be appreciated that the pivot connection between links allows for stowing the link parallel to the straight portion defined by the shaft and the barrel of the handle. In addition, various embodiments employ a unique and novel retraction assembly that enables the clinician to manually retract the firing rod and thus, the end effector firing bar, without the assistance of springs or other force generating members that may be employed to apply a retraction force to the firing drive. Such additional force generating devices, while helpful when retracting the firing rod, require the instrument to generate firing forces that must also overcome the forces generated by such additional retraction force generating members. Thus, the various retraction systems disclosed herein are said to generate the "sole" retraction motion or force. This means that the retraction motions/forces are generated by manipulation of the various retraction members by the clinician without any assistance from additional springs or force generating members.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container.

The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument, comprising:
   a handle assembly;
   an end effector for performing a surgical operation, said end effector operably coupled to said handle assembly and operably supporting a firing member that is movable from a retracted position to a fired position in response to a longitudinal firing motion applied thereto;
   a firing drive supported by said handle assembly and configured to selectively generate said longitudinal firing motion upon actuation of a firing trigger operably coupled to said handle assembly; and
   a retraction assembly supported by said handle assembly and interfacing with said firing drive such that manual actuation of said retraction assembly causes said firing drive to generate a sole retraction motion which is communicated to said firing member to cause said firing member to move from said fired position to said retracted position.

2. The surgical instrument of claim 1 further comprising at least one indication member operably supported on said handle assembly and interfacing with said firing drive to provide a visual indication of the progress of the firing member during the application of said firing motion and sole retraction motion to said end effector.

3. The surgical instrument of claim 1 further comprising:
   a closure drive supported by said handle assembly and configured to generate a closing motion and an opening motion; and
   an elongate shaft assembly coupling said end effector to said handle assembly and configured to transfer said opening and closing motions and said firing and retraction motions thereto.

4. The surgical instrument of claim 3 wherein said end effector comprises:
   an elongate channel coupled to said elongate shaft assembly and being sized to receive a staple cartridge therein; and
   an anvil coupled to said elongate channel and being selectively movable between open and closed positions in response to open and closing motions from said elongate shaft assembly and wherein said firing member comprises a cutting and severing member operably supported within said elongate channel and being responsive to said firing and retraction motions from said elongate shaft assembly.

5. The surgical instrument of claim 3 wherein said closure drive comprises:
   a locking mechanism for automatically locking said closure drive in a locked position after said closure drive has fully applied said closing motion to said end effector; and
   a release mechanism interfacing with said locking mechanism to selectively apply an unlocking motion thereto.

6. The surgical instrument of claim 5 wherein said locking mechanism interfaces with said firing drive such that said locking mechanism prevents actuation of said firing drive unless said closure drive is in said locked position.

7. The surgical instrument of claim 1 wherein said firing drive comprises:
   a linked rack operably supported by said handle assembly;
   a firing rod communicating with said linked rack and said end effector for transmitting said firing and retraction motions thereto; and
   a firing trigger operably supported by said handle assembly and configured to interact with said linked rack such that actuation of said firing trigger causes said linked rack to apply said firing motion to said firing rod.

8. The surgical instrument of claim 7 wherein said retraction assembly comprises a retraction member operably supported by said handle assembly, said retraction member communicating with said linked rack such that manual actuation of said retraction member causes said linked rack to apply said sole retraction motion to said firing rod.

9. The surgical instrument of claim 8 further comprising at least one retraction gear operably supported by said handle assembly and interfacing with said retraction member and said linked rack.

10. The surgical instrument of claim 8 wherein said retraction member is movable between a first position corresponding to said unfired position and a second position corresponding to said fired position and wherein said retraction member is moved from said first position to said second position as said firing trigger is actuated and wherein said retraction member is moved from said second position to said first position upon application of a retraction force to said retraction member.

11. A surgical instrument comprising:
    a handle assembly;
    an end effector for performing a surgical operation, said end effector operably coupled to said handle assembly and operably supporting a firing member that is movable from a retracted position to a fired position in response to a longitudinal firing motion applied thereto and from said fired position to said retracted position upon application of a retraction motion thereto;
    a linked rack operably supported by said handle assembly;
    a firing rod communicating with said linked rack and said end effector for transmitting said firing and retraction motions from said linked rack to said end effector;
    a firing trigger operably supported by said handle assembly and configured to interface with said linked rack such that actuation of said firing trigger causes said linked rack to apply said firing motion to said firing rod;
    a first gear in meshing engagement with said linked rack; and
    a retraction lever movably supported by said handle assembly and configured to interface with said first gear such that actuation of said retraction lever applies a sole retraction motion to said first gear which thereby transfers said sole retraction motion to said linked rack.

12. The surgical instrument of claim 11 further comprising a second gear selectively couplable to said retraction lever and in meshing engagement with said first gear.

13. The surgical instrument of claim 12 wherein said retraction lever is selectively coupled to said second gear by a retraction pawl that selectively engages a portion of said second gear when said retraction lever is pivoted in a first direction and disengages said portion of said second gear when said second gear is pivoted in a second direction.

14. The surgical instrument of claim 13 further comprising:
a closure drive supported by said handle assembly and configured to generate a closing motion and an opening motion;
an elongate shaft assembly coupling said end effector to said handle assembly and configured to transfer said opening and closing motions from said closure drive to said end effector; and
a locking mechanism for automatically locking said closure drive in a locked position after said closure drive has fully applied said closing motion to said end effector, said locking mechanism interfacing with said second gear to prevent actuation thereof unless said closure drive is in said locked position.

15. A surgical instrument comprising:
a handle assembly;
an end effector for performing a surgical operation, said end effector operably coupled to said handle assembly and operably supporting a firing member that is movable from a retracted position to a fired position in response to a longitudinal firing motion applied thereto and from said fired position to said retracted position upon application of a retraction motion thereto;
a first linked rack operably supported by said handle assembly;
a firing rod communicating with said linked rack and said end effector for transmitting said firing and retraction motions from said linked rack to said end effector;
a firing trigger operably supported by said handle assembly and configured to selectively interface with said linked rack such that actuation of said firing trigger causes said linked rack to apply said firing motion to said firing rod;
a second gear rack operably supported by said handle assembly;
a drive gear in meshing engagement with said first linked rack and said second gear rack; and
a retraction lever movably coupled to said handle assembly and said second gear rack such that actuation of said retraction lever applies a sole retraction motion to said drive gear which thereby transfers said sole retraction motion to said linked rack.

16. The surgical instrument of claim 15 further comprising:
a closure drive supported by said handle assembly and configured to generate a closing motion and an opening motion;
an elongate shaft assembly coupling said end effector to said handle assembly and configured to transfer said opening and closing motions from said closure drive to said end effector; and
a locking mechanism for automatically locking said closure drive in a locked position after said closure drive has fully applied said closing motion to said end effector, said locking mechanism interfacing with said second gear rack to retain said second gear rack in a second locked position to prevent actuation thereof unless said closure drive is in said locked position.

17. The surgical instrument of claim 16 further comprising a release mechanism interfacing with said locking mechanism to selectively apply an unlocking motion thereto.

18. The surgical instrument of claim 16 wherein said retraction lever has a grip portion that is adjacent the handle assembly when said firing member is in said retracted position and wherein said grip portion is spaced away from said handle assembly when said firing member is in said fired position.

19. The surgical instrument of claim 15 wherein said retraction lever has a grip portion and is movable from a first position wherein said grip portion is adjacent said handle assembly and a second position wherein said grip portion is spaced away from said handle assembly.

* * * * *